(12) United States Patent
Brown

(10) Patent No.: US 8,095,340 B2
(45) Date of Patent: Jan. 10, 2012

(54) HOME POWER MANAGEMENT SYSTEM

(75) Inventor: Stephen J. Brown, Woodside, CA (US)

(73) Assignee: Health Hero Network, Inc., Palo Alto, CA (US)

(*) Notice: Subject to any disclaimer, the term of this patent is extended or adjusted under 35 U.S.C. 154(b) by 1525 days.

(21) Appl. No.: 11/487,282

(22) Filed: Jul. 14, 2006

(65) Prior Publication Data
US 2006/0271214 A1 Nov. 30, 2006

Related U.S. Application Data

(63) Continuation-in-part of application No. 11/272,816, filed on Nov. 15, 2005, now Pat. No. 7,613,590.

(51) Int. Cl.
G06F 11/00 (2006.01)

(52) U.S. Cl. ............. 702/188; 702/1; 702/57; 702/104; 702/189

(58) Field of Classification Search ............... 702/1, 57, 702/104, 188, 189; 700/90, 286; 340/3.1, 340/500
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi et al. |
| 3,883,235 A | 5/1975 | Lynn et al. |
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |

(Continued)

FOREIGN PATENT DOCUMENTS

EP 0286456 10/1988

(Continued)

OTHER PUBLICATIONS

Albisser, A.M. "Intelligent Instrumentation in Diabetic Management", CRC Critical Reviews in Biomedical Engineering, vol. 17, No. 1, pp. 1-24, 1989.

(Continued)

*Primary Examiner* — Mohamed Charioui
*Assistant Examiner* — Elias Desta
(74) *Attorney, Agent, or Firm* — Christopher P. Maiorana, PC

(57) ABSTRACT

Systems and methods for managing power usage are provided. The system includes a programmable microprocessor, at least one input mechanism, a memory having instructions and/or other information, a display, at least one power consuming power device and a remote server. The systems allows the user of a power consuming device to receive instructions or other information from the server. The method includes using stored program instructions to generate power device related information on a display, collecting power device data representative of the electrical current or power consumed, connecting to a remote computing facility having a server, and providing the data to a computer remotely located from the central server.

20 Claims, 12 Drawing Sheets

U.S. PATENT DOCUMENTS

| | | |
|---|---|---|
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |
| 5,339,821 A | 8/1994 | Fujimoto |
| 5,341,291 A | 8/1994 | Roizen et al. |
| 5,343,239 A | 8/1994 | Lappington et al. |
| 5,344,324 A | 9/1994 | O'Donnell et al. |
| 5,357,427 A | 10/1994 | Langen et al. |
| 5,366,896 A | 11/1994 | Margrey et al. |
| 5,368,562 A | 11/1994 | Blomquist et al. |
| 5,371,687 A | 12/1994 | Holmes, II et al. |
| 5,375,604 A | 12/1994 | Kelly et al. |
| 5,377,100 A | 12/1994 | Pope et al. |
| 5,390,238 A | 2/1995 | Kirk et al. |
| 5,399,821 A | 3/1995 | Inagaki et al. |
| 5,410,471 A | 4/1995 | Alyfuku et al. |
| 5,410,474 A | 4/1995 | Fox |
| 5,429,140 A | 7/1995 | Burdea et al. |
| 5,431,690 A | 7/1995 | Schaldach et al. |
| 5,431,691 A | 7/1995 | Snell et al. |
| 5,434,611 A | 7/1995 | Tamura |
| 5,438,607 A | 8/1995 | Przygoda, Jr. et al. |
| 5,438,983 A | 8/1995 | Falcone |
| 5,441,047 A | 8/1995 | David et al. |
| 5,449,334 A | 9/1995 | Kingsbury |

| Patent | Date | Inventor |
|---|---|---|
| 5,454,721 A | 10/1995 | Kuch |
| 5,454,722 A | 10/1995 | Holland et al. |
| 5,456,606 A | 10/1995 | McIntyre |
| 5,456,692 A | 10/1995 | Smith, Jr. et al. |
| 5,458,123 A | 10/1995 | Unger |
| 5,467,269 A | 11/1995 | Flaten |
| 5,471,039 A | 11/1995 | Irwin, Jr. et al. |
| 5,471,382 A | 11/1995 | Tallman et al. |
| 5,483,276 A | 1/1996 | Brooks et al. |
| 5,488,412 A | 1/1996 | Majeti et al. |
| 5,488,423 A | 1/1996 | Walkingshaw et al. |
| 5,500,561 A * | 3/1996 | Wilhelm .................. 307/64 |
| 5,501,231 A | 3/1996 | Kaish |
| 5,502,636 A | 3/1996 | Clarke |
| 5,502,726 A | 3/1996 | Fischer |
| 5,504,519 A | 4/1996 | Remillard |
| 5,517,405 A | 5/1996 | McAndrew et al. |
| 5,518,001 A | 5/1996 | Snell |
| 5,519,058 A | 5/1996 | Gonick et al. |
| 5,519,433 A | 5/1996 | Lappington et al. |
| 5,523,232 A | 6/1996 | Sechler |
| 5,536,249 A | 7/1996 | Castellano et al. |
| 5,542,420 A | 8/1996 | Goldman et al. |
| 5,544,649 A | 8/1996 | David et al. |
| 5,546,943 A | 8/1996 | Gould |
| 5,549,117 A | 8/1996 | Tacklind et al. |
| 5,550,575 A | 8/1996 | West et al. |
| 5,553,609 A | 9/1996 | Chen et al. |
| 5,558,638 A | 9/1996 | Evers et al. |
| 5,564,429 A | 10/1996 | Bornn et al. |
| 5,569,212 A | 10/1996 | Brown |
| 5,572,421 A | 11/1996 | Altman et al. |
| 5,572,646 A | 11/1996 | Kawai et al. |
| 5,574,828 A | 11/1996 | Hayward et al. |
| 5,576,952 A | 11/1996 | Stutman et al. |
| 5,583,758 A | 12/1996 | McIlroy et al. |
| 5,590,648 A | 1/1997 | Mitchell et al. |
| 5,593,349 A | 1/1997 | Miguel et al. |
| 5,593,390 A | 1/1997 | Castellano et al. |
| 5,594,637 A | 1/1997 | Eisenberg et al. |
| 5,596,994 A | 1/1997 | Bro |
| 5,597,307 A | 1/1997 | Redford et al. |
| 5,601,435 A | 2/1997 | Quy |
| 5,613,495 A | 3/1997 | Mills et al. |
| 5,619,991 A | 4/1997 | Sloane |
| 5,624,265 A | 4/1997 | Redford et al. |
| 5,628,309 A | 5/1997 | Brown |
| 5,629,981 A | 5/1997 | Nerlikar |
| 5,631,844 A | 5/1997 | Margrey et al. |
| 5,633,910 A | 5/1997 | Cohen |
| 5,635,532 A | 6/1997 | Samid |
| 5,640,569 A | 6/1997 | Miller et al. |
| 5,640,953 A | 6/1997 | Bishop et al. |
| 5,642,731 A | 7/1997 | Kehr |
| 5,642,936 A | 7/1997 | Evans |
| 5,651,363 A | 7/1997 | Kaufman et al. |
| 5,651,775 A | 7/1997 | Walker et al. |
| 5,659,691 A | 8/1997 | Durward et al. |
| 5,666,487 A | 9/1997 | Goodman et al. |
| 5,670,711 A | 9/1997 | Detournay et al. |
| 5,675,635 A | 10/1997 | Vos et al. |
| 5,678,562 A | 10/1997 | Sellers |
| 5,678,571 A | 10/1997 | Brown |
| 5,679,075 A | 10/1997 | Forrest et al. |
| 5,680,590 A | 10/1997 | Parti |
| 5,680,866 A | 10/1997 | Kangas et al. |
| 5,687,322 A | 11/1997 | Deaton et al. |
| 5,687,717 A | 11/1997 | Halpern et al. |
| 5,687,734 A | 11/1997 | Dempsey et al. |
| 5,689,652 A | 11/1997 | Lupien et al. |
| 5,692,906 A | 12/1997 | Corder |
| 5,704,364 A | 1/1998 | Saltzstein et al. |
| 5,704,366 A | 1/1998 | Tacklind et al. |
| 5,704,902 A | 1/1998 | Vandenbelt et al. |
| 5,704,922 A | 1/1998 | Brown |
| 5,710,178 A | 1/1998 | Samid |
| 5,710,918 A | 1/1998 | Lagarde et al. |
| 5,711,297 A | 1/1998 | Iliff |
| 5,714,319 A | 2/1998 | Joutel et al. |
| 5,715,451 A | 2/1998 | Marlin |
| 5,715,823 A | 2/1998 | Wood et al. |
| 5,717,739 A | 2/1998 | Dyer et al. |
| 5,717,913 A | 2/1998 | Driscoll |
| 5,720,733 A | 2/1998 | Brown |
| 5,722,418 A | 3/1998 | Bro |
| 5,727,153 A | 3/1998 | Powell |
| 5,730,124 A | 3/1998 | Yamauchi |
| 5,730,654 A | 3/1998 | Brown |
| 5,732,696 A | 3/1998 | Rapoport et al. |
| 5,732,709 A | 3/1998 | Tacklind et al. |
| 5,734,413 A | 3/1998 | Lappington et al. |
| 5,749,083 A | 5/1998 | Koda et al. |
| 5,752,234 A | 5/1998 | Withers |
| 5,754,740 A | 5/1998 | Fukuoka et al. |
| 5,760,771 A | 6/1998 | Blonder et al. |
| 5,772,585 A | 6/1998 | Lavin et al. |
| 5,778,882 A | 7/1998 | Raymond et al. |
| 5,782,814 A | 7/1998 | Brown et al. |
| 5,785,650 A | 7/1998 | Akasaka et al. |
| 5,787,295 A | 7/1998 | Nakao |
| 5,791,342 A | 8/1998 | Woodard |
| 5,792,117 A | 8/1998 | Brown |
| 5,793,969 A | 8/1998 | Kamentsky et al. |
| 5,794,219 A | 8/1998 | Brown |
| 5,794,251 A | 8/1998 | Watanabe et al. |
| 5,796,393 A | 8/1998 | MacNaughton |
| 5,799,318 A | 8/1998 | Cardinal et al. |
| 5,800,458 A | 9/1998 | Wingrove |
| 5,802,494 A | 9/1998 | Kuno |
| 5,802,534 A | 9/1998 | Hatayama et al. |
| 5,806,057 A | 9/1998 | Gormley et al. |
| 5,810,747 A | 9/1998 | Brudny et al. |
| 5,819,735 A | 10/1998 | Mansfield et al. |
| 5,822,544 A | 10/1998 | Chaco et al. |
| 5,822,715 A | 10/1998 | Worthington et al. |
| 5,825,283 A | 10/1998 | Camhi |
| 5,827,180 A | 10/1998 | Goodman |
| 5,828,943 A | 10/1998 | Brown |
| 5,832,448 A | 11/1998 | Brown |
| 5,835,896 A | 11/1998 | Fisher et al. |
| 5,840,020 A | 11/1998 | Heinonen et al. |
| 5,842,976 A | 12/1998 | Williamson |
| 5,868,669 A | 2/1999 | Iliff |
| 5,868,683 A | 2/1999 | Protopapas et al. |
| 5,875,432 A | 2/1999 | Sehr |
| 5,879,163 A | 3/1999 | Brown et al. |
| 5,882,338 A | 3/1999 | Gray |
| 5,887,133 A | 3/1999 | Brown et al. |
| 5,893,077 A | 4/1999 | Griffin |
| 5,893,098 A | 4/1999 | Peters et al. |
| 5,897,493 A | 4/1999 | Brown |
| 5,899,855 A | 5/1999 | Brown |
| 5,911,687 A | 6/1999 | Sato et al. |
| 5,913,310 A | 6/1999 | Brown |
| 5,918,603 A | 7/1999 | Brown |
| 5,920,477 A | 7/1999 | Hofbert et al. |
| 5,933,136 A | 8/1999 | Brown |
| 5,935,060 A | 8/1999 | Iliff |
| 5,940,801 A | 8/1999 | Brown |
| 5,941,829 A | 8/1999 | Saltzstein et al. |
| 5,945,651 A | 8/1999 | Chorosinski et al. |
| 5,951,300 A | 9/1999 | Brown |
| 5,954,641 A | 9/1999 | Kehr et al. |
| 5,956,501 A | 9/1999 | Brown |
| 5,960,403 A | 9/1999 | Brown |
| 5,961,446 A | 10/1999 | Beller et al. |
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |

| | | | |
|---|---|---|---|
| 6,023,686 A | 2/2000 | Brown | |
| 6,024,281 A | 2/2000 | Shepley | |
| 6,029,138 A | 2/2000 | Khorasani et al. | |
| 6,032,119 A | 2/2000 | Brown et al. | |
| 6,035,328 A | 3/2000 | Soukal | |
| 6,046,761 A | 4/2000 | Echerer | |
| 6,049,794 A | 4/2000 | Jacobs et al. | |
| 6,050,940 A | 4/2000 | Braun et al. | |
| 6,055,314 A | 4/2000 | Spies et al. | |
| 6,055,487 A | 4/2000 | Margery et al. | |
| 6,055,506 A | 4/2000 | Frasca, Jr. | |
| 6,057,758 A | 5/2000 | Dempsey et al. | |
| 6,068,615 A | 5/2000 | Brown et al. | |
| 6,095,985 A | 8/2000 | Raymond et al. | |
| 6,101,478 A | 8/2000 | Brown | |
| 6,110,148 A | 8/2000 | Brown et al. | |
| 6,113,578 A | 9/2000 | Brown | |
| 6,115,698 A * | 9/2000 | Tuck et al. | 705/37 |
| 6,138,145 A | 10/2000 | Kawanaka | |
| 6,144,837 A | 11/2000 | Quy | |
| 6,151,586 A | 11/2000 | Brown | |
| 6,161,095 A | 12/2000 | Brown | |
| 6,167,362 A | 12/2000 | Brown et al. | |
| 6,167,386 A | 12/2000 | Brown | |
| 6,168,563 B1 | 1/2001 | Brown | |
| 6,177,940 B1 | 1/2001 | Bond et al. | |
| 6,186,145 B1 | 2/2001 | Brown | |
| 6,189,029 B1 | 2/2001 | Fuerst | |
| D439,242 S | 3/2001 | Brown et al. | |
| 6,210,272 B1 | 4/2001 | Brown | |
| 6,221,012 B1 | 4/2001 | Maschke et al. | |
| 6,233,539 B1 | 5/2001 | Brown | |
| 6,240,393 B1 | 5/2001 | Brown | |
| 6,248,065 B1 | 6/2001 | Brown | |
| 6,260,022 B1 | 7/2001 | Brown | |
| 6,270,455 B1 | 8/2001 | Brown | |
| 6,270,456 B1 | 8/2001 | Iliff | |
| 6,334,778 B1 | 1/2002 | Brown | |
| 6,352,523 B1 | 3/2002 | Brown et al. | |
| 6,368,273 B1 | 4/2002 | Brown | |
| 6,370,513 B1 | 4/2002 | Kolawa et al. | |
| 6,375,469 B1 | 4/2002 | Brown | |
| 6,379,301 B1 | 4/2002 | Worthington et al. | |
| 6,381,577 B1 | 4/2002 | Brown | |
| 6,436,036 B1 | 8/2002 | Miller-Kovach et al. | |
| 6,513,532 B2 | 2/2003 | Mault et al. | |
| 7,761,910 B2 * | 7/2010 | Ransom et al. | 726/6 |
| 2002/0019748 A1 | 2/2002 | Brown | |
| 2004/0106855 A1 | 6/2004 | Brown | |
| 2004/0107116 A1 | 6/2004 | Brown | |
| 2004/0117207 A1 | 6/2004 | Brown | |
| 2004/0117208 A1 | 6/2004 | Brown | |
| 2004/0117209 A1 | 6/2004 | Brown | |
| 2004/0117210 A1 | 6/2004 | Brown | |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 199540709596 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

Billiard, A., et al. "Telematic Transmission of Computerized Blood Glucose Profiles for IDDm Patients", Diabetes Care, (Feb. 1991), vol. 14, No. 2, pp. 130-134.

Blood Glucose Monitors, Portable Health Device, (1998), vol. 17(9), pp. 253-271.

Horio, Hiroyuki, et al., "Clinical Telecommunication Network System for Home Monitoring", Medical & Biological Engineering & Computing, (Mar. 1994), vol. 32, 227-230.

Hunter, "Technological Advances in Bedside Monitoring: Biosensors", Archives and Laboratory Medicine, (Jul. 1987), pp. 633-636.

Introducing the Next Generation of About Your Diabetes, U.S. Pharmacopical Convention and American Diabetes Association, (1993).

Jimison et al., "Patient-Specific explanation in models of chronic disease", Revised Feb. 1992 Artificial Intelligence in Medicine 4 (1992) 191-205.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Latman, N.S., "Evaluation of Electronic, Digital Blood Glucose Monitors", Biomedical Instrumentation and Technology, (1991), vol. 25, No. 1, 43-49.

Makikawa, M., et al., "Microprocessor-Based Memory Device for Ambulatory Heart Rate and Physical Activity Recording", Methods of Information in Medicine, (1994), vol. 33, No. 1, pp. 94-96.

Miles, Laughton E., "A Portable Microcomputer for Long-Term Physiological Monitoring in the Home and Work Environment", Medical Monitoring in the Home and Work Environment, (1990), pp. 47-57.

Pfeiffer, E. F., "The Glucose Sensor: The Missing Link in Diabetes Therapy", Hormone and Metabolic Research, (1990), vol. 24m Suppl. pp. 154-164.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Reis, H, "Telemedicine: Transmitting Expertise to the Point of Care Toward an Electronic Patient Record"; '97, Nashville, TN, Apr. 27-May 3, 1997, pp. 248-256, v. 3.

+5V Powered Isolated RS-232 Drivers/Receivers Maxim Integrated Products, 1989.

Adilman; "Videogames: Knowing the Score"; Creative Computing; v9; p. 224(5); Dec. 1983; Dialog: File 148, Acc# 01891055.

AdOptimizer—Ad Management Software for Websites, Newsbytes, pNEW10040041, Oct. 4, 1996.

Anonymous, "Health Hero Network, Inc. Receives First-Ever FDA Clearance for Connecting Medical Devices to Internet", PR Newswire, (Dec. 2, 1993), 3 pages.

Antique Collector , Putting the Lot on the Net, vol. 66, Issue 9, p. 26, Downloaded from Corporate Resource Net, Nov./Dec. 1995.

Bai, "Design of home healthcare network", IEEE 1997 pp. 1657-1658.

Bower, "Brain Clues to Energy-efficient Learning", Science News, (Apr. 1992), v. 141; p. 215(1); Dialog: File 647, Acct# 12123949.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bruce, "Health Hero Network CEO, CNNfn", Digital Jam, (Dec. 1, 1999), 3.

Bruce, et al., "The Effects of Sympathetic Nervous System Activation and Psychological Stress . . . "; Diabetologia; 35(9); 1992; 835-843; Dialog: File 5, Acc#9629427. (9 pages).

Brunetti, P., et al., "A Simulation Study on a Self-Turning Portable Controller of Blood Glucose", The International Journal of Artificial Organs, (1993), Vol. 16, No. 16, pp. 51-57.

Caprihan, A., et al., "A Simple Microcomputer for Biomedical Signal Processing", IECI '78 Annual Conference Proceedings on Industrial Applications of Microprocessors, (Mar. 20, 1978), 18-23.

Cathay Pacific Airways-USA receives more than 1,300 bids during first five days of CyberAuction; Business Wire, Oct. 18, 1995, p. 10181119.

Cathay Pacific Airways-USA to Hold First-Ever Internet CyberAuction; CyberTravelers Can Bid for 50 Business Class Round Trips to Hong Kong—No Minimum Bid; Business Wire; p. 9261084; Sep. 26, 1995; Dialog: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Cheng, Joe H., "PCT Search Report", (Jan. 11, 1996).

DigiPet Instruction Manual, 1997.

Digital Doggie; retrieved from URL http://www.virtualpet.com/vp/farm/gigapet/ddoggie.htm Apr. 23, 2000.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p. 1(3); Nov. 8, 1995; Dialog: File 148, Acc#08289119.

EP European Search Report, From 6858P005EP, (Mar. 27, 1998).

Fabietti, RG., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; p. 26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Future of the Virtual Pet Industry, 1997 [retrieved on Apr. 23, 2000], Retrieved from <URL:www.virtualpet.com/vp/ future/future.htm>.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giga Farm; retrieved from URL http://www.virtualpet.com/vp/farm/gigapet/gpfarm/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Gordon; "Auctions Become High Tech"; Dealer Business; v29 n7; p. 21(4); Mar. 1995; Dialog: File 148, Acc#07862519.

Guiffrida, et al., Should We Pay the Patient? Review of Financial Incentives to enhance Patient Compliance:, Biomedical Journal, (1997), vol. 315, pp. 703-707.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hutheesing, Nikhil, "An on-line gamble", Forbes, v157 n10 p. 288(1), May 20, 1996.

Jaffrey et al.; "PIN: An Associated Protein Inhibitor of Neuronal Nitric Oxide Synthase"; Science; vol. 274; Nov. 1, 1996; Ref: XP 002050141.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Lachnit, Carroll, "Hawkin's Online Auction", Photo District News, vol. 16, Issue 1, p. 18, Jan. 1996.

Lacyk, John, "PCT Search Report", (Jun. 12, 1997).

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Meissner, et al., "Building an Integrated Clinical and Research Network", Proceedings of the SPIE, (Oct. 24, 1995), vol. 2618, p. 92-99.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Nano Page, 1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's at it Again"; Bond Buyer; v309 n29448; p. 1(3); Jul. 21, 1994; Dialog: File 148, Acc#07478152.

Onsale Joins Fray as Online Shopping Picks Up Speed: Internet Booms; Computer Reseller News; Jun. 5, 1995; p. 73; Dialog: File 16, Acc#05649796.

Onsale Onsale Brings Thrill of Auctions and Bargain Hunting Online; Unique Internet retail service debuts with week-long charity auction for the Computer Museum in Boston, May 24, 1995; Dialog Abstract: File 610, Acc#0489267.

Playmates Toys deals knockout blow to virtual pet competitors with introduction of Nano Fighter™ for Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducing talking Nano Pals; Talking Nano Pet Press Release; Nov. 18, 1997; retrieved from URL http://www.virtualpet.com/vp/farm/nano/talkn/tnpress.htm on Apr. 23, 2000.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", Sensors, (Feb. 1994), pp. 12-20.

Research project launched to improve health of America's communities; new Disney community in Florida is focus of program. Business Wire, p10011142. Oct. 1, 1996.

Results of the world's first on-line auction, http://www.christies.com, Dec. 27, 1995.

RO_AUCTION Auctioneers Property Database System and RO_AUCTION Auctioneers Accounting System; RO-AUCTION features; Dec. 4, 1995.

Roberts; "Diabetes and Stress: A Type A Connection?", Psychology Today, (Jul. 1987), v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.saveearth. Auction Web, http://www.ebay.com, Dec. 27, 1995.

Schement, "An Intelligent Controller for Neurophysiological Experiments," Proceeding of the Annual Symposium on Computer Based Medical Systems, Durham, Jun. 14-17, 1992, p. 528, line 1-p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Seigmann;"Nowhere to Go but Up"; PC Week; v12 n42, p. A5(1); Oct. 23, 1995; Dialog: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate the Desktop in the 90's?", , Electronics, Feb. 1990, pp. 48-50. (3 pages).

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Skolnick et al. "Simultaneous Analysis of Multiple Polymorphic Loci Using Amplified Sequence Polymorphisms (ASPs)"; Genomics. 2: 273-279, May 18 , 1988.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal of Nursing Research, v18, n2, p. 136(13), Apr. 1996.

Symbol Technologies; "Healthcare Mobility Solutions for the PPT8800", Feb. 2004.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/lleg.htm>.

Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.

Telemedicine Provides Two-Way Computer Link for Parents of Very Premature Infants. PR Newswire. p1007NEM034. Oct. 7, 1996.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

United Healthcare's OPTUM Division goes online to better health by announcing a unique internet application. PR Newswire, p0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Virtual Pet Product Reviews, 1997 [retrieved on Apr. 23, 2000], Retrieved from <URL:www.virtualpet.com/vp/farm/reviews/reviews,html>.

Virtual Tomagutchi, 1998 [retrieved Apr. 23, 2000], Retrieved from <URL:www.sttf.org/english/action/tomagutchi.html>.

Voelker, Rebecca, "Shoe Leather Therapy is Gaining on TB", JAMA, (Mar. 13, 1996), vol. 275, 743.

Wilkins, Aaron. "Expanding Internet access for health care consumers", Health Care Management Review, Summer, Jul. 1999, 24-30.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

* cited by examiner

HOME POWER MANAGEMENT SYSTEM

This application is a continuation in-part of Ser. No. 11/272,816, filed Nov. 15, 2005, now U.S. Pat. No. 7,613,590. T*he above-identified* application is incorporated herein by reference in its *entirety*.

The present application is related to U.S. Pat. Nos. 6,168,563; 6,101,478; 5,897,493; 5,307,263; 5,899,855; 6,381,577; 6,248,065; and 6,368,273, which are hereby incorporated by reference in their entirety.

BACKGROUND

1. Field of the Invention

The invention is generally directed to power monitoring and in particular to a microprocessor-based power monitoring system in which the power devices may be connected to a computer network.

2. Description of the Related Art

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

In recent years appliances that include microchips have been developed. These "smart appliances" can be programmed by their owners to turn themselves on or off, even when the owners are not present. Smart coffee makers can start brewing coffee before the owner is even awake. Sophisticated thermostats allow for the input of multiple programs, for example, different weekday and weekend schedules. These devices provide both convenience and energy savings.

Smart homes have been suggested. That is, a home in which many, if not all, of the appliances have microchips and are networked to a central computer in the house. In this way, tremendous control over the various household appliances can be realized by the owner, resulting in significant energy savings. Although these various smart appliances give their owner much control, they have not been networked or connected in any way to a remotely located professional associated with a utility supplying power or third party (i.e., non-consumer, non-supplier) such as an entity involved in regulating power or some other party with an expertise in power monitoring or power management.

Presently, there is a need for a power monitoring system that networks or connects appliances in a home or business to a remotely located professional or third party. It would be advantageous to have a power monitoring system in which an expert could assist the owner/operator in maximizing energy savings. It would also be advantageous to have a system in which this could be accomplished interactively in real time or near real time. It would be further advantageous to have a system in which the expert could send educational or even advertising information to the owner/operator. Additionally, it would be advantageous to have a system in which some or all of the appliances could be controlled remotely.

SUMMARY OF THE INVENTION

The present invention provides a system for managing power usage by at least one power consumer comprising: a programmable microprocessor; at least one input mechanism; a memory having instructions and/or other information; a display; at least one device having at least one sensor operable for monitoring the electrical current or power consumption associated with operation of the device and for producing signals representative of the monitored electrical current or power consumed; a communications device connectable in signal communication with both the programmable microprocessor and the at least one monitor; and program instructions for the programmable microprocessor that, (i) cause instructions and/or other information stored in the memory to be presented to the power consumer on the display, (ii) collect data from a user interaction with the at least one input mechanism in response to the display and store data in memory, (iii) collect data from the at least one sensor and store the data in memory, (iv) transmit data to a remotely located server, (v) receive from the server instructions and/or other information stored on the server for transmission to the programmable microprocessor, wherein the instructions and/or other information facilitate changes in the power consumer's behavior through consumer education and/or feedback based on the collected data, and (vi) store instructions and/or other information in the memory.

The present invention also provides a method of using a modular microprocessor system for managing power usage by a power consumer comprising: (a) at a site employing at least one device, (i) using stored program instructions to generate device related information on at least one display; (ii) collecting device data representative of the electrical current or power consumed thereby using a programmable microprocessor; (b) connecting at least one remotely located computing facility including at least one central server for communication with a communications device at the device site; and (c) providing the data to at least one computer remotely located from and in signal communication with the central server, wherein hardware and software of the central server are configured to receive and store device-related data from the device site that can be viewed or retrieved by an authorized user from the remotely located computer.

The present invention also provides a system for remotely monitoring a device, the system comprising: a) a server; b) a remote interface for entering in the server a set of queries; and c) a remotely programmable apparatus for interacting with the device, the remotely programmable apparatus being in communication with the server; wherein the server comprises: i) a script generator for generating a script program from the set of queries and a profile, the script program being executable by the remotely programmable apparatus to communicate the set of queries to the power consumer, to receive responses to the set of queries, and to transmit the responses from the remotely programmable apparatus to the server; and ii) a database connected to the script generator, the database for storing the script program, the responses to the set of queries, and the power consumer profile; and wherein the remotely programmable apparatus comprises: i) a communication device for receiving the script program from the server and for transmitting the responses to the server; ii) an interface for communicating the set of queries to the power consumer and for receiving the responses to the set of queries; iii) a memory for storing the script program and the responses to the set of queries; and iv) a processor connected to the communication device, the interface, and the memory for executing the script program to communicate the set of queries to the power consumer, to receive the responses to the set of queries, and to transmit the responses to the server.

The present invention also provides a system for managing power usage comprising: a plurality of networked customer sites having, a programmable microprocessor; at least one input mechanism; a memory having instructions and/or other information; a display; at least one device having at least one sensor operable for monitoring the electrical current or power consumed associated with operation of the device and for producing signals representative of the monitored electrical current or power consumed; a communications device connectable in signal communication with both the programmable microprocessor and the at least one monitor; and program instructions for the programmable microprocessor that, (i) cause instructions and/or other information stored in the memory to be presented to a user on the display, (ii) collect data from a user interaction with the at least one input mechanism in response to the display and stores data in memory, (iii) collect data from the at least one sensor and stores the data in memory, (iv) transmit data to a remotely located server, (v) receive from the server instructions and/or other information stored on the server for transmission to the programmable microprocessor, and (vi) store instructions and/or other information in the memory, wherein the plurality of customer sites are configured to act as a virtual utility or power co-op.

The present invention also provides a method of using a modular microprocessor system for managing power usage comprising: (a) at a plurality of sites employing at least one device, (i) using stored program instructions to generate device related information on at least one display; (ii) collecting device related data using a programmable microprocessor; (b) connecting at least one remotely located computing facility including at least one central server for communication with a communications device at the device sites; (c) providing the device data to at least one computer remotely located from and in signal communication with the central server, wherein hardware and software of the central server are configured to receive and store device-related data from the plurality of device sites that can be viewed or retrieved by a user from the remotely located computer; and (d) aggregating the plurality of device sites into a virtual utility or power co-op.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

Figure 1:
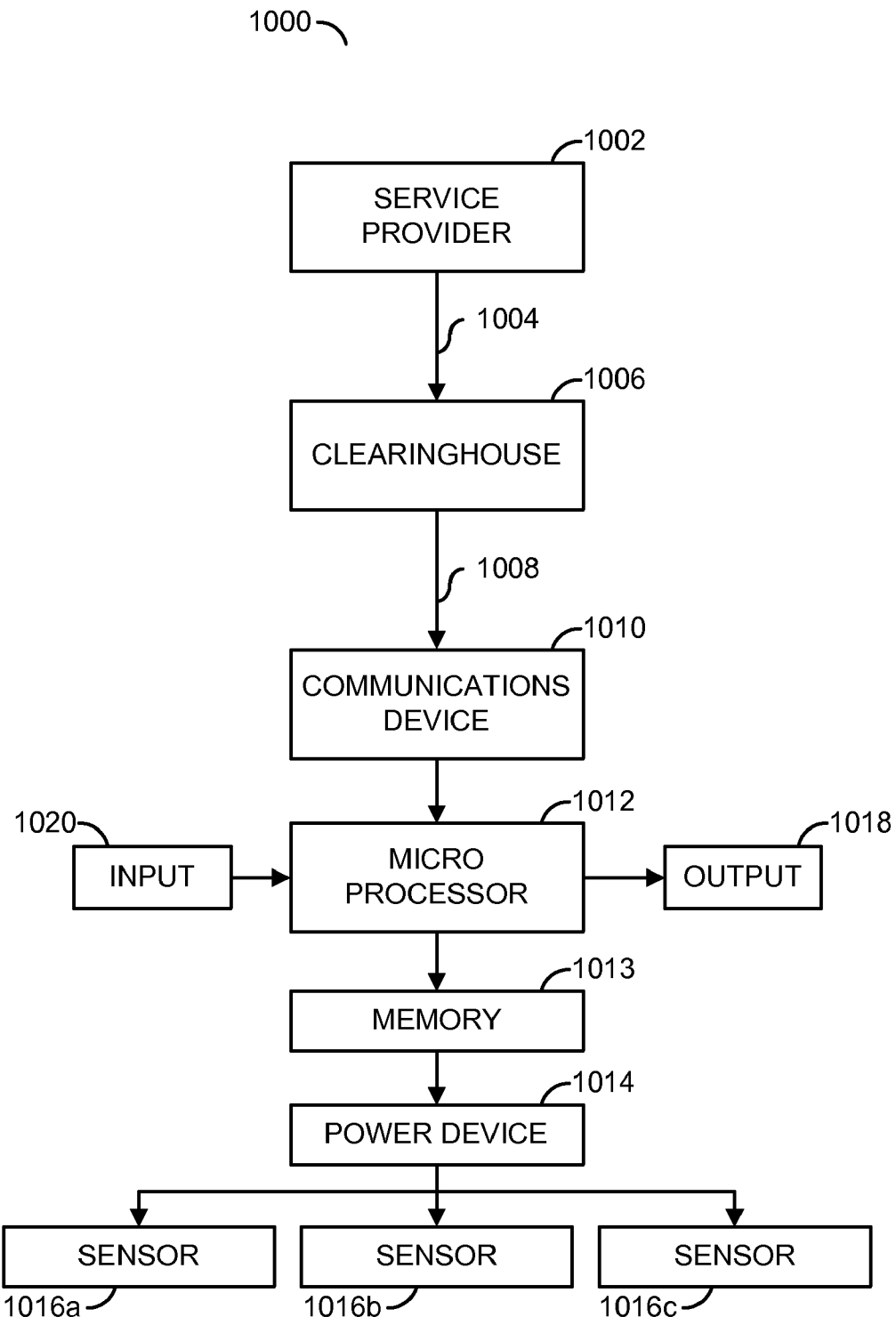
FIG. 1 is a schematic diagram of a power monitoring system according to one embodiment of the invention.

The present invention, in one embodiment, provides a modular power monitoring and management system. Other embodiments of the invention include methods of using power consuming devices (hereinafter "power devices") employing a modular power monitoring and management system. The system may employ a compact microprocessor-based device that includes switches for controlling operation of the device. The microprocessor-based device processes data supplied by sensors that can be integrated with the power devices to supply signals for displaying relevant information on a display that may be included in the microprocessor-based device or may be integrated into the power device. The sensors can collect data from the power device and the user's environment and send data to a clearinghouse or central server.

In one embodiment of the invention, data can be sent from a data management device to a remote clearinghouse having a server and from the server to a remotely located service provider. In this embodiment, the system provides for transmission of signals to the remote clearinghouse including, for example, via telephone lines or other transmission media. Preferably, the clearinghouse includes signal processing capability for transmission of reports to the remotely located service provider and for transmission of program instructions to the data management device for adaptation of the power device. The service provider is preferably a professional associated with a utility supplying power. However, the service provider may also be a third party (i.e., non-consumer, non-supplier) such as an entity involved in regulating power or some other party with an expertise in power monitoring or power management. In one embodiment of the invention, the third party may independently verify power usage. In some embodiments of the invention, any or all of the power consumer, the power supplier and the third party may have to authenticate themselves before using the power monitoring system. In still other embodiments, the power consumer, the power supplier and/or the third party have different levels of access to the system. In further embodiments of the invention a consumer profile is stored on the server. This profile may include an inventory of the power consumer's power devices, the consumer's preferences, and other data relevant to the consumer's consumption of power.

In one embodiment of the invention, the system includes a program cartridge operatively connected to the microprocessor-based device. The program cartridge adapts the microprocessor-based device for operation with various power devices such as stoves, ovens, lamps, overhead lights, air conditioners, televisions, as well as small appliances such as toasters, blenders, coffee makers, etc. In one aspect of the invention, a preprogrammed cartridge may be purchased, for example, at retail stores such as department stores, and the like. In another aspect of the invention, a preprogrammed cartridge can be ordered for delivery through the mail. These cartridges may be ordered, for example, from the device manufacturer, third party developers/designers, or utility customer service centers. In still another aspect of the invention, the adaptation can occur by downloading program instructions from the clearinghouse server to the cartridge. The program instructions may be selected by the user of the power device via a website or by the service providers. In other embodiments of the invention, program instructions sent from the clearinghouse reconfigure software in the program cartridge, altering the operation of the power device. In still another embodiment of the invention, the program cartridge is operatively connected to the power device via a receptacle in the power device. In this embodiment, the program cartridge adapts the power device to supply signals for displaying relevant information on a display that may be included in the microprocessor-based device or may be integrated into the power device.

In other embodiments, the functionality of the cartridge is incorporated directly into the microprocessor-based device. In still other embodiments, the functionality of the cartridge is incorporated in a memory integrated in the power device. In all of the above-embodiments, program instructions may be downloaded from the clearinghouse server to adapt or reconfigure the microprocessor or the power device.

FIG. 1 illustrates a modular microprocessor-based tool system 1000 according to one embodiment of the invention. In this embodiment, a service provider 1002 is in signal connection with a clearinghouse 1006, e.g., via a network 1004. The service provider 1002 may be, for example, a power management system, a professional associated with a utility supplying power or an entity involved in regulating power.

In this embodiment, the clearinghouse 1006 includes a central server (not shown) that includes memory for storing instructions and messages from the service provider 1002 as well as data and questions/messages from the operator of the power device 1014. In other embodiments of the invention, the central server includes software that allows it to analyze data from the power device 1014. Thus, in these embodiments, the clearinghouse is capable of transferring both "raw" data, that is unprocessed data from the power device 1014, as well as analyzed data. The analysis software may include statistical analysis tools as well as tools to graphically represent the data.

The clearinghouse 1006 is connected to the power device 1014, e.g., via a network 1008. The first and second networks 1004, 1008 have been illustrated as different networks to aid in describing the flow of information between the service provider 1002 and the power devices 1014. However, some or all parts of the networks 1004, 1008 may be the same. That is, data and information may, for example, flow over the Internet as part of networks 1004, 1008.

Figure 3:
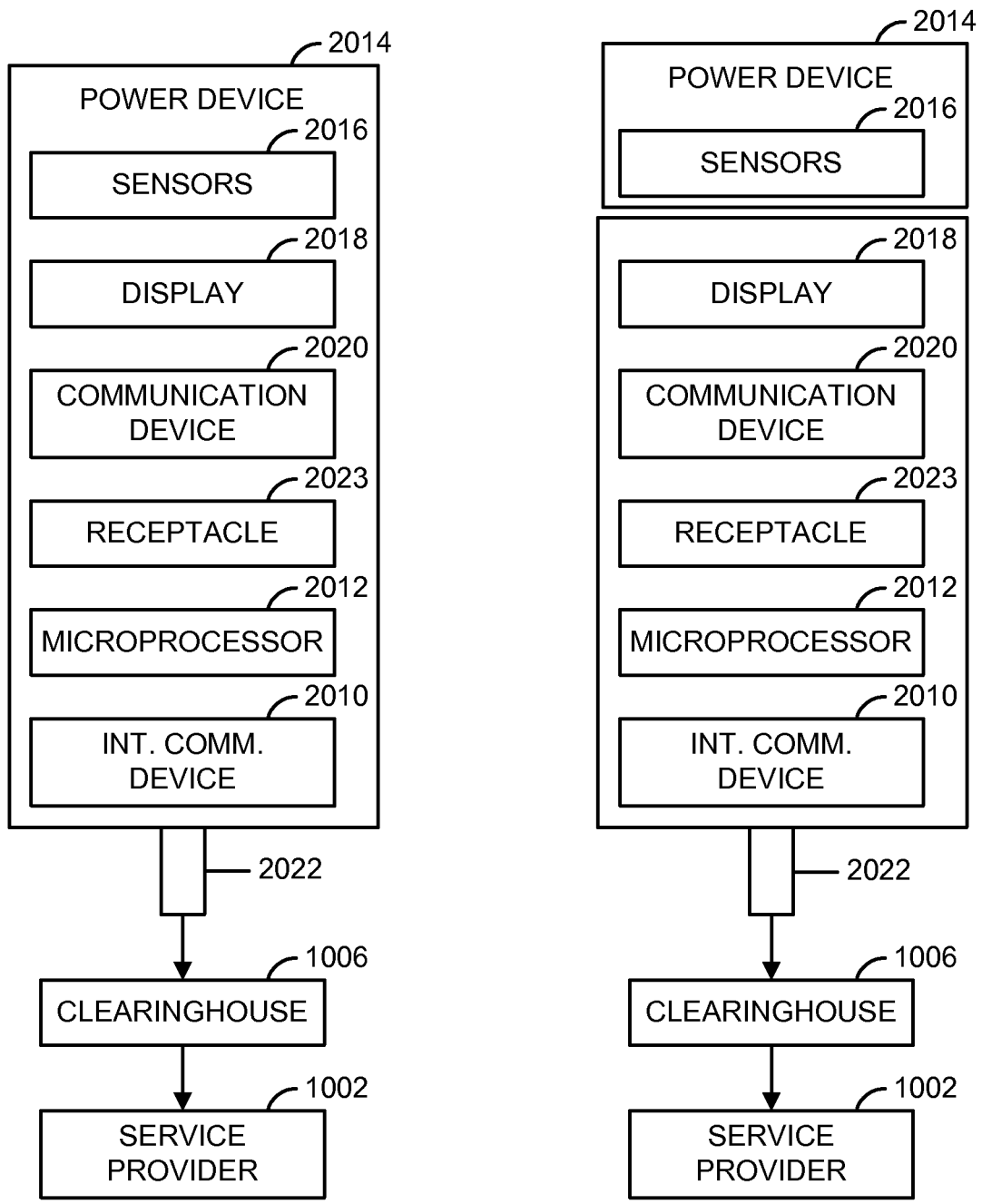
FIG. 3 is a side view of a power device according to an embodiment of the invention.

The connection between the second network 1008 to the power device 1014 may be through a communications device 1010 and a microprocessor 1012. In one embodiment of the invention, the communications device 1010 and the microprocessor 1012 are housed in a data management device (not shown in FIG. 1). In one aspect of this embodiment, the data management device is a handheld unit (discussed in more detail below). The communications device 1010 may be, for example, a modem. In other embodiments of the invention, the communications device 1010 and the microprocessor 1012 may be integral with the power device 2014 (FIG. 3).

The modular microprocessor-based device system 1000 may also include a memory 1013. This memory 1013 may also be integral with the power device 1014 or located within the aforementioned handheld unit. Preferably the memory 1013 stores program instructions that aid in the operation of the power device 1014 as well as coordinate the collection of data from sensors 1016a-1016c. Additionally, the memory 1013 can store sensor data and messages from the operator to the service provider 1002 and from the service provider 1002 to the operator.

Also depicted in FIG. 1 is an input mechanism 1020 and an output mechanism 1018. In one embodiment of the invention, the input mechanism can comprise a plurality of buttons or switches that allow the user to answer questions or input information related to the operation of the power device 1014. Other input mechanisms may also be used. For example touch screens, light pens and miniature keyboards may also be used. The output mechanism can be, for example, a display screen that can display both text and graphics. Audio output devices are also contemplated.

Associated with one or more power device 1014 are sensors 1016a-1016c. As illustrated in FIG. 1, the power device 1014 has three sensors 1016a-1016c. This is by way of example only. The power device 1014 may have any number of sensors 1016. In one embodiment of the invention, the sensors 1016a-1016c are integral with the power device 2014 (see FIG. 3). In other embodiments of the invention, one or more of the sensors 1016 may be external of the power device 1014 but capable of measuring relevant data. For example, the sensors 1016 may be part of a smart electrical socket (not shown). In one embodiment of the invention, the smart socket may be hard wired into the wall, that is, replace the standard wall socket. In another embodiment of the invention, the smart socket is a separate unit that is plugged into a standard socket and receives the plug of a power devices. The one more external sensors 1016 may measure, for example, ambient temperature or relative humidity. The internal sensor 1016 may be used to measure, for example, current, power consumption, ambient temperature or any other property useful for determining if the device should be turned on, off, or be varied. As an example, a measurement of the ambient temperature may be used to determine if an air conditioner or heater should be increased or decreased. The sensors 1016 are in signal communication with at least one of the microprocessor 1012 and the memory 1013.

Figure 2:
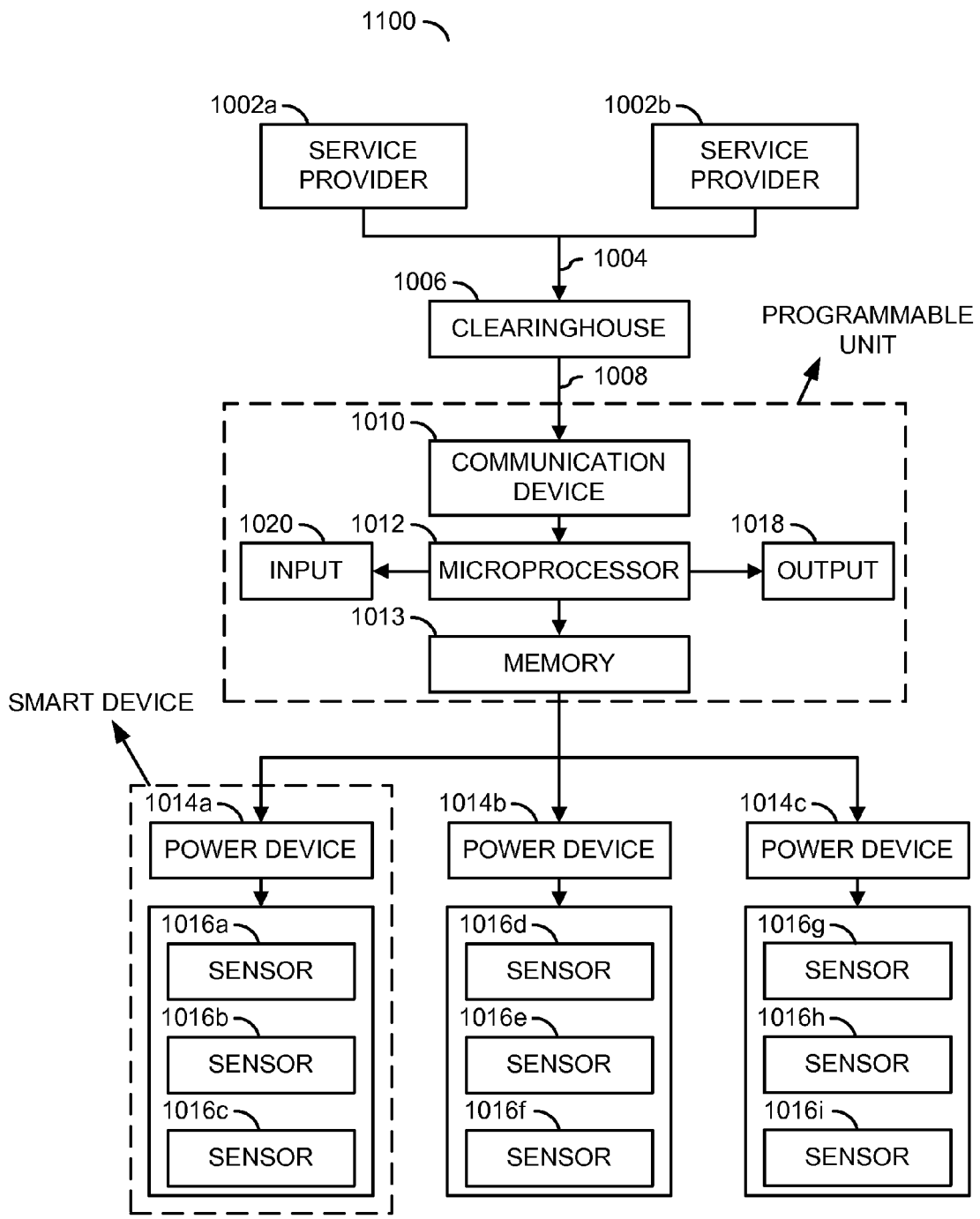
FIG. 2 is a schematic diagram of a power monitoring system according to another embodiment of the invention.

FIG. 2 illustrates another embodiment of the invention. The modular microprocessor-based power monitoring system 1100 of this embodiment may include more than one service provider(s) 1002a, 1002b. In the illustrated embodiment, there are two service providers 1002a, 1002b. However, there may be any number of service providers 1002.

As evident from the illustrated embodiment, the invention may include multiple power devices 1014a, 1014b, 1014c. FIG. 2 illustrates three power devices 1014a, 1014b, 1014c, however, any number of power devices 1014 may be included. This embodiment is suitable, for example, a home in which many power devices (e.g., refrigerator, freezer, heating, air conditioning) are in constant or frequent use. Other examples include, commercial, business and industrial settings in which many power devices 1014 are typically in use. Each of the power devices 1014a, 1014b, 1014c has been illustrated with three sensors 1016a-1016c. As in the earlier embodiments, there may be more or less than three sensors per power device 1014. Further, there may be any combination of service providers 1002, power devices 1014 and sensors 1016. The example illustrated in FIG. 2 is merely for illustrative purposes only.

FIG. 3 illustrates a power device 2014 constructed according to one embodiment of the invention. In this embodiment, the power device 2104 includes integral sensors 2016. Further, this embodiment includes an integral microprocessor 2012 and an integral communications device 2010. The integral communications device 2010 may be a modem or a wireless transmitter. In one aspect of the invention, communications can be affected by sending a signal through the power cord 2022. In another aspect of the invention, a separate communications port (not shown) adapted to receive a communications cable can be provided. In still another aspect of the invention, the communications device 2010 is a wireless transmitter/receiver.

The power device 2014 of this embodiment of the invention also includes an output device such as a display 2018. Preferably, the display 2018 can illustrate graphics as well as alphanumeric text. The power device 2014 may also include audible or tactile output devices (not shown). Also included are input devices 2020. As illustrated, input devices 2020 are push buttons. Alternative input devices 2020 include touch screens and switches. Further, it is contemplated that an entire miniature keyboard may be included. With the input device 2020, the power device operator can respond to questions and comments from the service provider 1002 and even input questions for the service provider 1002. Thus, both data and messages can be sent back and forth from the power device 2014 operator to the service provider 1002 via the clearinghouse 1006. The data may include "raw" data, that is, unanalyzed data. However, in some embodiments of the invention, the power device 2014 is also provided with memory (not shown) and software that can analyze the sensor data. Thus, the service provider 1002 can be provided with both raw and analyzed data. In still other embodiments of the invention, the power device 2014 is provided with a receptacle 2023 adapted to receive a program cartridge (not shown). In this embodiment, the program cartridge may include the instructions to adapt the power device 2014 to operate in the power device system. That is, the program cartridge may include instructions for operating the sensors 2016, the microprocessor 2012, the communications device 2010, the display 2018 and the input devices 2020.

In another embodiment of the invention, a plurality of homes, businesses, or combinations thereof may be aggregated or pooled to from a virtual utility or power co-op. Because several entities are pooled together, the virtual utility may be able to negotiate with the local utility for better prices. In this way, financial returns may be optimized. Preferably, the virtual utility or co-op can negotiate based on managed consumption and/or predictable usage patterns. Optionally, the pooled power consuming sites may be metered as a group. Further, the virtual utility or co-op can negotiate for rolling-blackout management rather than a total blackout in a power shortage. With the system and methods of the present invention, rolling-blackout management may be accomplished by blocking out specific local usages. In one embodiment of the invention, preferences to specific local usages may be designated by each power consumer. For example, a particular power consumer may upload into his consumer profile a preference to some power consuming devices be turned downed or even turned completely off while others continue to get full power.

In one embodiment, preferences may be set by ranking all of the networked power consuming devices. In an alternate embodiment, rather than give each power consuming device a unique ranking, categories of importance may be established. In this embodiment, several power consuming devices may have the same ranking. In this manner, in times of power shortage, individual power consuming devices may turned off by a utility rather than shutting off all of the power to a neighborhood.

Alternate embodiments of the invention contemplate that one or more power consumers may operate power generating devices. Possible power generating devices include, but are not limited to, solar units, wind turbines, geothermal units, fuel cells, biofuels, or exercise equipment. Power from the power generating devices may be supplied to the power grid. The supplier of power may optionally have their power meter rolled back, be sent a rebate check or be compensated by any other agreed to method. The supplied power may be "sold" individually or be aggregated and sold back collectively.

One example in which this method is advantageous is having the sever send recommendations on saving power through changing usage patterns or suggesting conservation tips. In another example, the server provides feedback and other information to the user on environmental factors, such as $CO_2$ emissions, that result from consumer usage patterns and/or decisions. In still another example, the server may include sponsorship and/or advertisements targeting the power consumer.

In one method of the practicing the invention the power device user can remotely control at least one power device 1014. This may be accomplished, for example, with a handheld device, described in more detail below. In other embodiments of the invention, the handheld device user can control a plurality of power devices 1014.

In still other embodiments of the invention, the system may include electronic storage which can store historical usage and cost data. The electronic storage may be located at the consumer site, the clearinghouse, the utility, or a third party location. Furthermore, electronic storage may be located at some or all of these locations. With the historical data, the various entities associated with the system may perform statistical analysis and look for energy consumption trends. Analysis may show, for example, that a particular power device is in need of repair or replacement. Alternatively, the utility or third party can transmit advertisements for new, more energy efficient power devices 1014 to the power consumer.

In still other embodiments of the invention, the microprocessor 1012 and the communications device 1010 are supplied in a separate unit (discussed in more detail below). In still other embodiments of the invention, the power device user may connect the power device 1014 to a personal computer (discussed in more detail below). The connection may be either direct or via the separate device. In this embodiment of the invention, the power device user may take advantage of the keyboard and mouse of the personal computer to input information into the system.

Figure 4:
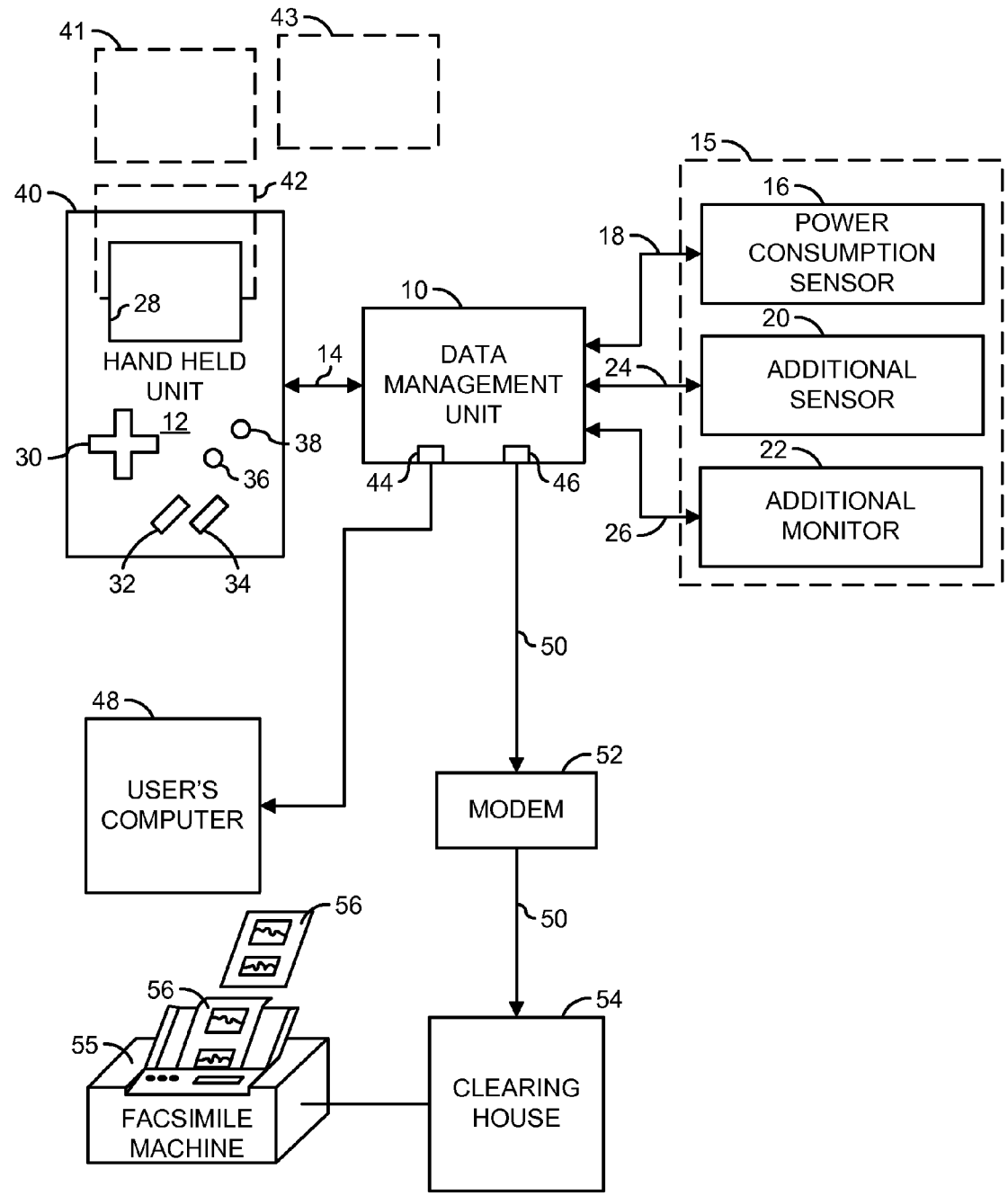
FIG. 4 is a schematic diagram of a power monitoring system according to a further embodiment of the invention.

FIG. 4 depicts a modular microprocessor-based power monitoring system arranged in accordance with another embodiment of the invention. In the arrangement shown in FIG. 1, a data management device 10 is electrically interconnected with a handheld microprocessor-based device 12 via a cable 14. In the depicted arrangement, data management device 10 also is in signal communication with a power device 15. The power device 15 may have a power consumption sensor 16 capable of sensing power consumed by the power device and producing an electrical signal representative thereof. Although FIG. 4 illustrates the power device 15 as being connected to data management device 10 by a cable 18, it may be preferable to construct power device 15 using wireless technology to provide signal communication between the power device 15 and the data management device 10. Example wireless technologies include, but are not limited to, cell phone, RF, and Bluetooth®. Regardless of the manner in which power device 15 is interconnected with data management device 10, both that interconnection and cable 14 can be configured for serial data communication between the interconnected devices. However, alternative date transfer schemes may be used.

Also shown in FIG. 4 are sensors 20 and 22, which are in data communication with data management device 10 via cables 24 and 26, respectively. Sensor 20 and sensor 22 of FIG. 4 represent sensors other than power consumption sensor 16 that can be used with the invention. Additional properties that may be monitored by the sensors include, but are not limited to humidity and room temperature. Upon understanding the various aspects and features of the invention it will be recognized that the invention is easily implemented for industrial and commercial, as well as home. Further, multiple sensors may be used with any given power device 15 and multiple power devices may be simultaneously monitored by the system. Sensors used in the practice of the invention can be arranged in a variety of ways. The data to be recorded or otherwise employed by handheld microprocessor device 12 and/or data management device 10 can be provided in serial format in synchronization with clock signals provided by data management device 10. The sensors 16, 20, 22 can be connected to data management device 10 with cables 18, 24, 26 (as shown in FIG. 4) or may be connected via wireless technology (not shown).

As is shown in FIG. 4, handheld microprocessor device 12 may include a display screen 28 and at least one input mechanism such as a plurality of switches or keys (30, 32, 34, 36, and 38 in FIG. 4), which are mounted on a housing 40. Located in the interior of housing 40, but not shown in FIG. 4, are a microprocessor, memory circuits, and circuitry that interface with switches 30, 32, 34, 36 and 38 with the microprocessor. Stored in the memory of program handheld microprocessor device 12 can be a set of program instructions that establishes a data protocol that allows handheld microprocessor device 12 to perform digital data signal processing and generate desired data or graphics for presentation on display 28 when a cartridge 42 is inserted in a slot or other receptacle in housing 40. That is, cartridge 42 of FIG. 4 may include any suitable or removable memory device, such as read-only memory units (or other memory means such as battery-powered random access memory) that store program instructions and/or data may adapt handheld microprocessor 12 for operation in modular microprocessor-based power device system. More specifically, when the instructions and/or data of cartridge 42 are combined with program instructions and data included in the internal memory circuits of handheld microprocessor device 12, handheld microprocessor device 12 is programmed for processing and displaying power device operational information in the manner described below. In each case, the plurality of switches or keys (30, 32, 34, 36, and 38 in FIG. 4) are selectively operated to provide signals that result in pictorial and/or alphanumeric information being displayed by display 28.

Various devices are known that meet the above-set forth description of handheld microprocessor device 12. For example, compact devices are available in which the plurality of keys allows alphanumeric entry and internal memory can be provided for storing information such as names, addresses, phone numbers, and an appointment calendar. Small cartridges or cards can be inserted in these devices to program the device for various purposes such as the playing of games, spreadsheet application, and foreign language translation sufficient for use in travel. More recently, less compact products that have more extensive computational capability and are generally called "palm top computers" have been introduced into the marketplace. These devices also can include provision for programming the device by way of an insertable card or cartridge. Alternatively, a handheld microprocessor device 12 can be provided with an internal memory (not removable) containing the necessary program instructions and/or data. An example of one such handheld microprocessor device is a mobile or cellular phone.

Certain embodiments of the invention are configured and arranged to operate in conjunction with yet another type of handheld microprocessor unit. Specifically, in these embodiments of the invention, cartridge 42 is electrically and physically compatible with commercially available compact video game systems, such as the system manufactured by Nintendo of America Inc. under the trademark "GAME BOY." Configuring data management device 10 and cartridge 42 for operation with a handheld video game system has several advantages. For example, the display of such a device provides display resolution that allows the invention to display both multi-line alphanumeric information and graphical data. In this regard, the 160×144 pixel dot matrix-type liquid crystal display screen currently used in the above-referenced compact video game systems provides sufficient resolution for at least six lines of alphanumeric text, as well as allowing graphical representation of statistical data such as graphical representation of heat or vibration generated by the power device 15.

Another advantage of providing handheld microprocessor device 12 in the form of a compact video game system is the relatively simple, yet versatile arrangement of switches that is provided by such a device. For example, as is indicated in FIG. 4, a compact video game system includes a control pad 30 that allows an object displayed on display 28 to be moved in a selected direction (i.e., up-down or left-right). As also is indicated in FIG. 4, compact video game systems typically provide two pair of distinctly shaped push button switches. In the arrangement shown in FIG. 4, a pair of spaced-apart circular push button switches (36 and 38) and a pair of elongate switches (32 and 34) are provided. The functions performed by the two pairs of switches is dependent upon the program instructions contained in each cartridge 42. The device illustrated in FIG. 4 is but one commercially available device. Any commercially available or proprietarily designed device having an alternative arrangement of buttons may be used.

Yet another advantage of utilizing a compact video game system for handheld microprocessor-based device 12 of FIG. 4 is the widespread popularity and low cost of such units. In this regard, manufacture and sale of a data management device 10, power device 15 with sensor 16 and cartridge 42 that operate in conjunction with a compact microprocessor-based video system allows the modular microprocessor-based power monitoring system of FIG. 4 to be manufactured and sold at a lower cost than could be realized in an arrangement in which handheld device 12 is designed and manufactured solely for use in the system of FIG. 4.

Another advantage of utilizing a compact video game system for handheld microprocessor-based device 12 of FIG. 4 is that power devices are increasingly being designed for children and used by children at home, as both toys and as child-versions of adult tools for construction and play. Integrating educational instructions, monitoring and feedback using a game system enables the least skilled users of power devices to gain an understanding of power consumption and conservation, as well as gain skills by learning to use tools for a variety of projects that can be loaded into the data management device 10 from the network or inserted with a cartridge 42.

An even further advantage of using a compact video game system for handheld microprocessor 12 is that such video game systems include means for easily establishing the electrical interconnection provided by cable 14 in FIG. 4. In particular, such compact video game systems include a connector mounted to the game device housing (40 in FIG. 4) and a cable that can be connected between the connectors of two video game units to allow interactive operation of the two interconnected units (i.e., to allow contemporaneous game play by two players or competition between players as they individually play identical but separate games). In certain embodiments of the invention, the "two-player" cable supplied with the compact video game device being used as handheld microprocessor device 12 is used as cable 14 to establish serial data communication between the handheld microprocessor device 12 (compact video game system) and data management device 10. In these embodiments, the program instructions stored on the memory of data management device 10 and cartridge 42 respectively program data management device 10 and the compact video game system (i.e., handheld microprocessor device 12) for interactive operation in which switches 30, 32, 34, 36 and 38 are used to control the operation of data management device 10 (e.g., to select a particular operational mode such as determining the optimal location of a cut or the display of statistical test data and, in addition, to control operation such as selection of an option during operation of the system in a particular operational mode). In each operational mode, data management device 10 processes data in accordance with program instructions stored in the memory circuits of data management device 10. Depending upon the operational mode selected by the user, data is supplied to data management device 10 by sensor 16, by additional sensors (20 and 22 in FIG. 4) or any interconnected computers or data processing facility (such as the hereinafter described user's computer 48 and clearinghouse 54 of FIG. 4). During such operation, mode switches 30, 32, 34, 36 and 38 are selectively activated so that signals are selectively coupled to the video game system (handheld microprocessor device 12) and processed in accordance with program instructions stored in cartridge 42. The signal processing performed by handheld microprocessor device 12 results in the display of alphanumeric, symbolic, or graphic information on the video game display screen (i.e., display 28 in FIG. 4), which allow the user to control system operation and obtain desired test results and other information.

With continued reference to FIG. 4, a data management device 10 of the invention may include a data port 44 that allows communication between data management device 10 and a personal computer 48 (or other programmable data processor). In certain embodiments of the invention, data port 44 is an RS-232 connection that allows serial data communication between data management device 10 and personal computer 48. In the practice of the invention, personal computer 48 can be used to supplement data management device 10 by, for example, performing more complex analyses of vibration and other data that has been supplied to and stored in the memory circuits of data management device 10. Alternatively, personal computer 48 can be used to supply data to data management device 10 that is not conveniently supplied by using handheld microprocessor switches 30, 32, 34, 36 and 38 as an operator interface to the system shown in FIG. 4. For example, some embodiments of the invention may employ a substantial amount of alphanumeric information that must be entered by the system user. Although it is possible to enter such data by using switches 30, 32, 34, 36 and 38 in conjunction with menus and selection screens displayed on display screen 28 of FIG. 4, it may be more advantageous to use a device such as personal computer 48 for entry of such data. However, if personal computer 48 is used in this manner, some trade-off of system features may be required because data management device 10 must be temporarily interconnected with personal computer 48 during these operations. That is, some loss of system mobility might result because a suitably programmed personal computer would be needed at each location at which data entry or analysis is to occur.

As is indicated in FIG. 4, a data management device 10 of the invention may also include a modem 52 that allows data communication between data management device 10 and a remote computing facility identified in FIG. 4 as clearinghouse 54 via a conventional telephone line (indicated by reference numeral 50 in FIG. 4) or by a wireless network. The modem 52 may be internal or external to the data management unit 10. As shall be described in more detail, clearinghouse computing facility 54 facilitates communication between a user of the system shown in FIG. 4 and professional service provider and can provide additional services such as updating system software. As is indicated by facsimile machine 55 of FIG. 4, one optional function of clearinghouse 54 is providing the professional service provider with standardized reports 56, which indicate both the current condition and condition trends of the system user. Although a single facsimile machine 55 is shown in FIG. 4, it will be recognized that numerous service providers (and hence facsimile machine 55) can be connected in signal communication with a clearinghouse 54.

Regardless of whether a compact video game system, another type of commercially available handheld microprocessor-based unit, a specially designed microprocessor device, or a microprocessor device integral with the power device 15, is used, embodiments of a modular microprocessor-based power monitoring system according to the present invention: (a) adapts a microprocessor device for displaying instructions for performing the monitoring and/or controlling a power device 15; (b) adapts a microprocessor device for displaying (graphically or alphanumerically) statistical data such as power usage or cost of power used; (c) adapts a microprocessor device for supplying control signals, signals representative room temperature, humidity, or other useful information, optionally to data management device 10; and, (d) adapts a microprocessor device for displaying information or instructions from a service provider that may be coupled to data management device 10 from a clearinghouse 54. The manner in which the arrangements of the present invention implement the above-mentioned functions and others can be better understood with reference to the illustrative embodiments of FIGS. 5 and 6.

Figure 5:
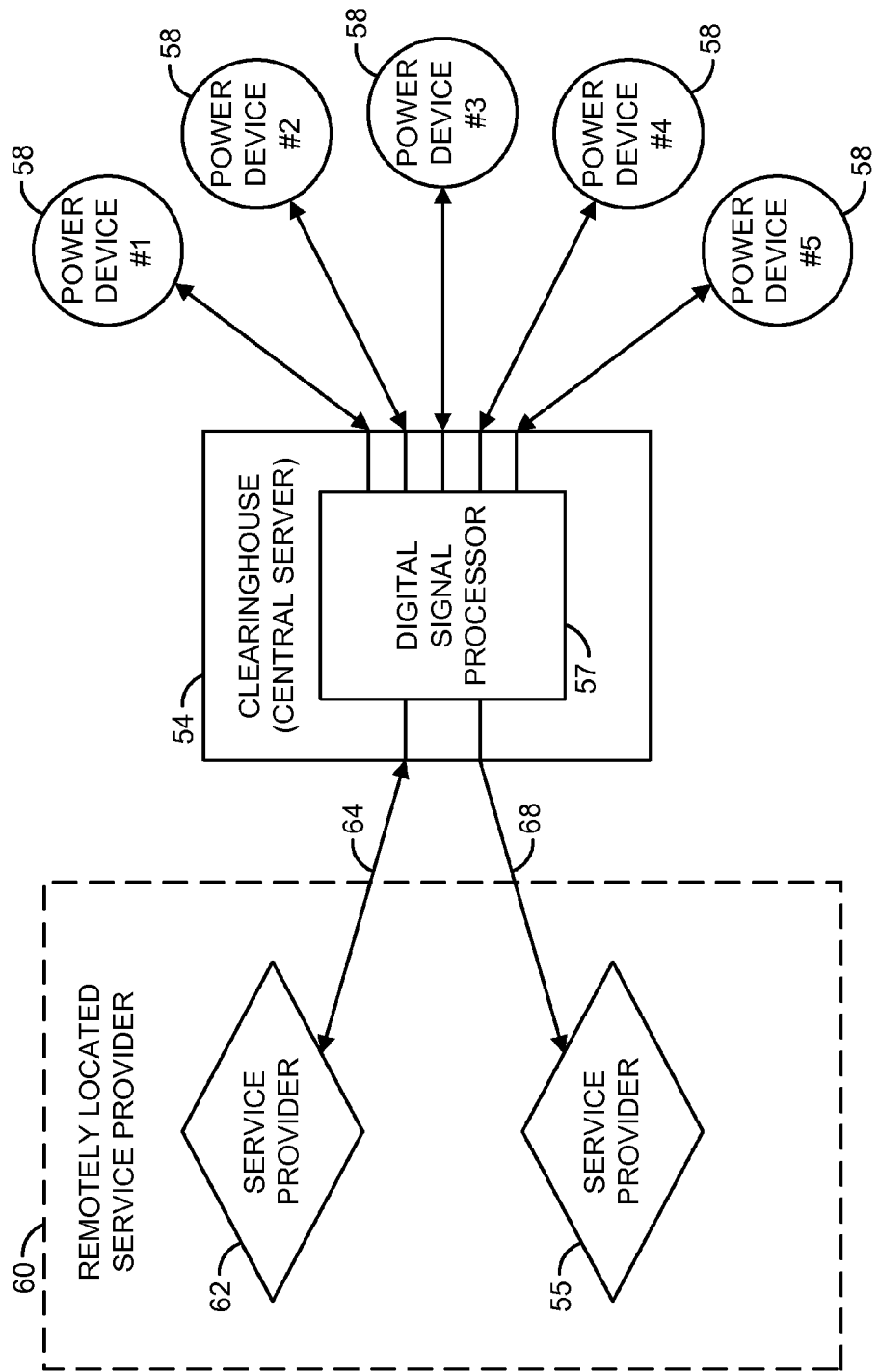
FIG. 5 is a schematic diagram of a power monitoring system according to another embodiment of the invention.

Referring first to FIG. 5, clearinghouse 54 receives data from one or more modular microprocessor-based power devices 15 of the type shown in FIG. 4. The data supplied to clearinghouse 54 by each individual modular microprocessor-based power device 15 may comprise "raw data," i.e., a parameter associated with the operation of the power devices 15 and related data that may be stored in memory circuits of the microprocessor device or a data management device 10, without further processing. For example, with respect to the arrangement shown in FIG. 4, power use and associated data such as room temperature and other such conditions are transmitted to clearinghouse 54 and stored with a digitally encoded signal that identifies both the source of the information (i.e., the power device) and those having access to the stored information (i.e., the system user's service providers).

As shall be recognized upon understanding the manner in which it operates, clearinghouse 54 can be considered to be a central server for the various system users and each service provider 60. In that regard, clearinghouse 54 includes conventionally arranged and interconnected digital processing equipment (represented in FIG. 5 by digital signal processor 57) which receives digitally encoded information from a user or service provider 60; processes the information as required; stores the information (processed or unprocessed) in memory if necessary; and, transmits the information to an intended recipient (i.e., user or service provider 60).

In FIG. 5, rectangular outline 60 represents one of numerous remotely located service providers who can utilize clearinghouse 54 and the arrangement described relative to FIGS. 1 and 2 in monitoring and controlling power device programs. Shown within outline 60 is a computer 62 (e.g., personal computer), which is coupled to clearinghouse 54 by means of a modem (not shown in FIG. 2) and a telephone line 64 or wireless network (not shown). Also shown in FIG. 5 is the previously mentioned facsimile machine 55, which is coupled to clearinghouse 54 by means of a second telephone line 68 or wireless network (not shown). Using the interface device of computer 62 (e.g., a keyboard or pointing device such as a mouse), the service provider can establish data communication between computer 62 and clearinghouse 54. Once data communication is established between computer 62 and clearinghouse 54, power device information can be obtained from clearinghouse 54 in a manner similar to the manner in which subscribers to various database services access and obtain information. In particular, the service provider can transmit an authorization code to clearinghouse 54 that identifies the service provider as an authorized user of the clearinghouse and, in addition, can transmit a signal representing the power device for which power device information is being sought. As is the case with conventional database services and other arrangements, the identifying data is keyed into computer 62 by means of a conventional keyboard (not shown in FIG. 5) in response to prompts that are generated at clearinghouse 54 for display by the display of computer 62 (not shown in FIG. 5).

Depending upon the hardware and software arrangement of clearinghouse 54 and selections made by the service provider via computer 62, power device information can be provided to the service provider in different ways. For example, computer 62 can be operated to access data in the form that it is stored in the memory circuits of clearinghouse 54 (i.e., raw data that has not been processed or altered by the computational or data processing arrangements of clearinghouse 54). Such data can be processed, analyzed, printed and/or displayed by computer 62 using commercially available or custom software. On the other hand, various types of analyses may be performed by clearinghouse 54 with the results of the analyses being transmitted to the remotely located service provider 60 and/or system user. For example, clearinghouse 54 can process and analyze data in a manner identical to the processing and analysis provided by the power monitoring system of FIG. 5. With respect to such processing and any other analysis and processing provided by clearinghouse 54, results expressed in alphanumeric format can be sent to computer 62 via telephone line 64 and the modem associated with computer 62, with conventional techniques being used for displaying and/or printing the alphanumeric material for subsequent reference.

The arrangement of FIG. 5 also represents one possible arrangement that allows the service provider to send messages and/or instructions to each power device 15 via computer 62, telephone line 64, and clearinghouse 54. The messages may be educational or may include feedback to the user as to how the power device is performing. In particular, clearinghouse 54 can be programmed to generate a menu that is displayed by computer 62 and allows the service provider to select a mode of operation in which information is to be sent to clearinghouse 54 for subsequent transmission to a user of the system described relative to FIGS. 1-4. This same menu (or related submenus) can be used by the service provider to select one or more modes of operation of the above-described type in which either unmodified power device data or the results of data that has been analyzed by clearinghouse 54 is provided to the service provider via computer 62 and/or facsimile machine 55.

In the contemplated embodiments of the present invention the user of the power device 15 can be provided with messages or instructions on modifying the settings of the power device 15. Transmitting messages is similar to the operation that allows the service provider to access data sent by a power device, i.e., transmitted to clearinghouse 54. The process differs in that the service provider 60 enters or selects the desired message or instruction via the keyboard or other interface device of computer 62. Once the message or instruction is entered and transmitted to clearinghouse 54, it is stored for subsequent transmission to the user for whom the information or instruction is intended. It should be understood that it is within the scope of the present invention that such messages or instructions can compromise a number of standard pre-composed messages or instructions that can be manually entered or automatically selected from a menu or list. These standard messages or instructions can optionally be selected based, at least in part, on the data collected from the power device 15. If, for example, the power device is a home power tool used for home improvement projects, then education or project management information can be sent based on the project design, the design parameters and the scaling factors or a materials and cut list may be generated for the end user. Based on the equipment and materials, settings are set to server and are then transmitted directly to the power device 15 or via the handheld microprocessor unit 12 and/or the data management device 10.

With respect to transmitting stored messages or instructions to a user of the invention, at least two techniques are available. The first technique is based upon the manner in which operational modes are selected in the practice of the invention. Specifically, in certain embodiments of the invention, program instructions that are stored in memory cause the system to generate menu screens that are displayed. The menu screens allow the system user to select the basic mode in which the system of is to operate and, in addition, allow the user to select operational subcategories within the selected mode of operation. Various techniques are known to those skilled in the art for displaying and selecting menu items. For example, in the practice of this invention, one or more main menus can be generated and displayed which allow the system user to select operational modes that may include: (a) a monitor mode (e.g., monitoring of heat generation); (b) a display mode (e.g., displaying previously obtained heat generation results, the service record, or other relevant information); (c) an input mode (e.g., a mode for entering data such as providing information that relates to power settings and user preferences; and, (d) a communications mode (for establishing a communication link with a remote computing facility such as clearinghouse 54 of FIG. 4).

In embodiments of the invention that employ a compact video game system for a handheld microprocessor device 12, the selection of menu screens and the selection of menu screen items preferably can be accomplished in substantially the same manner as menu screens and menu items are selected during the playing of a video game. For example, the program instructions stored in data management device 10 and cartridge 42 of the arrangement of FIG. 4 can be established so that a predetermined one of the compact video game switches (e.g., switch 32 in FIG. 4) allows the system user to select a desired main menu in the event that multiple main menus are employed. When the desired main menu is displayed, operation by the user of control pad 30 allows a cursor or other indicator that is displayed on the menu to be positioned adjacent to or over the menu item to be selected. Activation of a switch (e.g., switch 36 of the depicted handheld microprocessor device 12) causes the handheld microprocessor device 12 and/or data management device 10 to initiate the selected operational mode or, if selection of operational submodes is required, causes handheld microprocessor device 12 to display a submenu.

In view of the above-described manner in which menus and submenus are selected and displayed, it can be recognized that arrangements of the present invention can be configured and arranged to display a menu or submenu item that allows the user to obtain and display messages or instructions that have been provided by a service provider and stored in clearinghouse 54. For example, a submenu that is generated upon selection of the previously mentioned communications mode can include submenu items that allow the user to select various communication modes, including a mode in which serial data communication is established with clearinghouse 54, and a message status request is transmitted to clearinghouse 54. When this technique is used, the data processing system of clearinghouse 54 is programmed to search the clearinghouse memory to determine whether a message exists for the user making the request. Any messages stored in memory for that user are then transmitted to the user and processed for display or other output device. If no messages exist, clearinghouse 54 transmits a signal that causes the display or other output device to indicate "no messages." In this arrangement, clearinghouse 54 preferably is programmed to store a signal indicating that a stored message has been transmitted to the intended recipient (user). Storing such a signal allows the service provider to determine that messages sent to clearinghouse 54 for forwarding to a power device user have been transmitted to that power device user. In addition, program instructions allow the system user to designate whether received messages and instructions are to be stored in the memory for subsequent retrieval or review. In addition, in some instances it may be desirable to program clearinghouse 54 so that the service provider can designate (i.e., flag) information such as changes in operating conditions that will be prominently displayed to the user (e.g., accompanied by a blinking indicator) and stored in the memory regardless of whether the system user designates the information for storage.

A second technique that can be used for forwarding messages or instructions to a user does not require the system user to select a menu item requesting transmission by clearinghouse 54 of messages that have been stored for forwarding to that user. In particular, clearinghouse 54 can be programmed to operate in a manner that either automatically transmits stored messages for that user when the user operates the system or programmed to operate in a manner that informs the user that messages are available and allows the user to access the messages when he or she chooses to do so.

Practicing the invention in an environment in which the service provider uses a personal computer in some or all of the above-discussed ways can be very advantageous. On the other hand, the invention may also provide service providers timely information about system users without the need for a computer or any equipment other than a conventional facsimile machine (55 in FIGS. 4 and 5), or similar output device capable of receiving signals over a wired or wireless network, and presenting the information to the service provider. For example, information provided to clearinghouse 54 by a system user 15 can be sent to a service provider 60 via telephone line 68 and facsimile machine 55, with the information being formatted as a standardized graphic or textual report (56 in FIG. 4). Formatting a standardized report 56 (i.e., analyzing and processing data supplied by power device 16 or other system monitor or sensor) can be effected either by data management device 10 or within the clearinghouse facility 54. Moreover, various standardized reports can be provided. Preferably, the signal processing arrangement included in clearinghouse 54 allows each service provider 60 to select which of several standardized reports will be routinely transmitted to the service providers' facsimile machine 55 or other output device, and, to do so on a power device-by-power device (user-by-user) basis.

Figure 6:
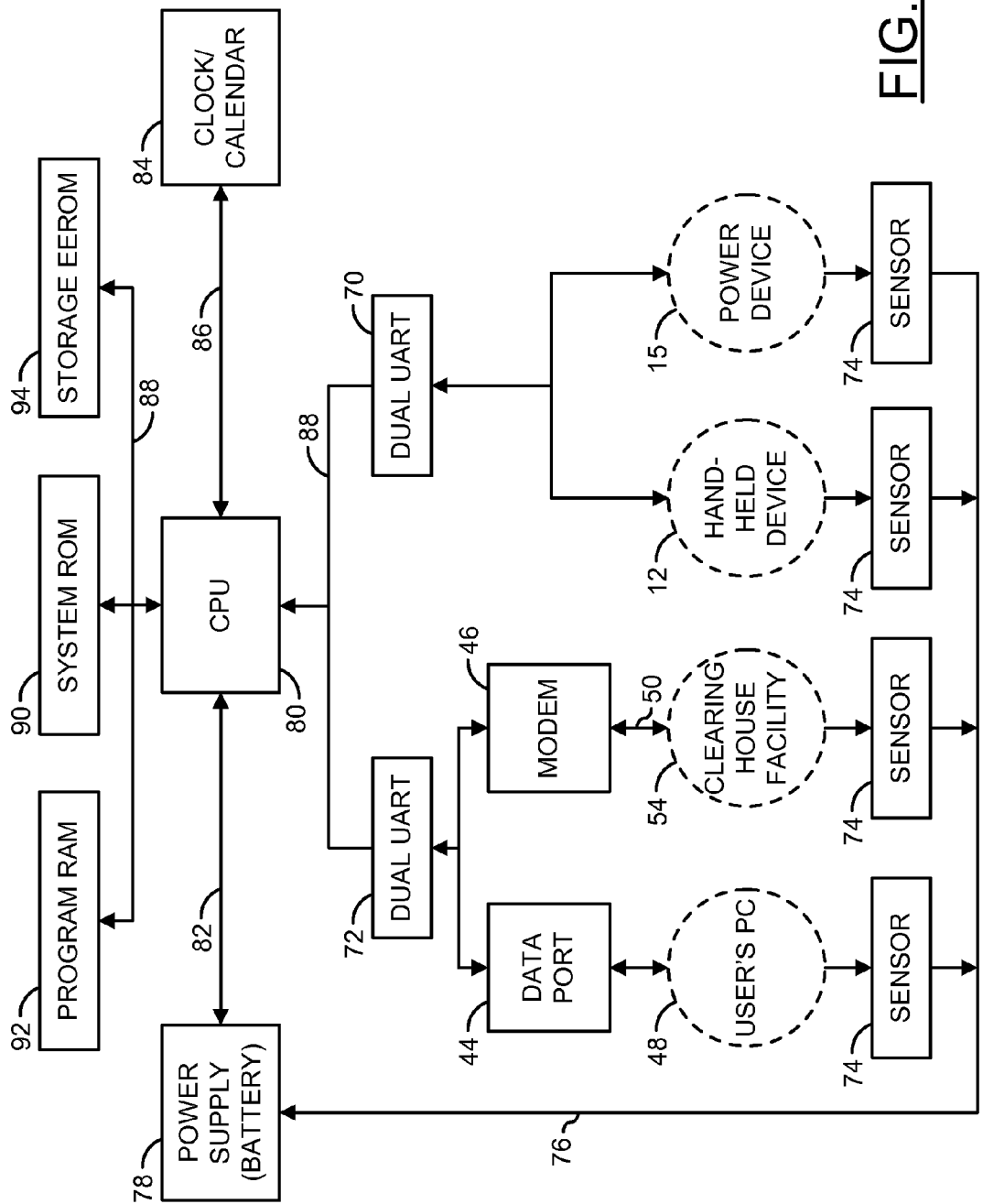
FIG. 6 is a schematic diagram illustrating structural components of a data management device and its connection to other components of the power device system.

FIG. 6 illustrates one embodiment of a manner in which various system components are arranged and interconnected with other system components for affecting the above-described operational aspects of the invention. As is symbolically indicated in FIG. 6, microprocessor device 12 and power device 15 are electrically connected to a dual universal asynchronous receiver transmitter 70 (by any suitable means such as cables 14 and 18). As also is indicated in FIG. 4 when a system user connects a personal computer 48 (or other programmable digital signal processor) to data port 44, signal communication is established between personal computer 48 and a second dual universal asynchronous receiver transmitter 72. Additionally, dual universal asynchronous receiver transmitter 72 is coupled to a communications device such as a modem 46 so that data communication can be established with a remote clearinghouse 54.

One embodiment includes a plurality of signal sensors 74, with at least one individual signal sensor being associated with each power device. As previously discussed, and as is indicated in FIG. 6, these devices may include handheld microprocessor device 12, power device 15, personal computer 48, remote computing facility 54 and, in addition, other additional power devices 15. Each signal sensor 74 is electrically connected for receiving a signal that will be present when the device with which that particular signal sensor is associated therewith and, in addition, is energized (e.g., turned on). For example, in previously mentioned embodiments of the invention in which data port 44 is an RS-232 connection, the signal sensor 74 that is associated with personal computer 48 can be connected to an RS-232 terminal that is supplied power when a personal computer is connected to data port 44 and the personal computer is turned on. In a similar manner, the signal sensor 74 that is associated with clearinghouse 54 can be connected to modem 46 so that the signal sensor 74 receives an electrical signal when modem 46 is interconnected to a remote computing facility (e.g., clearinghouse 54 of FIG. 5) via a telephone line 50.

In the arrangement of FIG. 6, each signal sensor 74 is preferably a low power switch circuit (e.g., a metal-oxide semiconductor field-effect transistor circuit), which automatically energizes data management device 10 whenever any one (or more) of the devices are associated with signal sensors 74 and is energized. Thus, as is indicated in FIG. 6 by signal path 76, each signal sensor 74 is interconnected with power supply 78, which supplies operating current and typically consists of one or more small batteries (e.g., three AAA alkaline cells).

The microprocessor and other conventional circuitry that enables processing system signals in accordance with stored program instructions is indicated in FIG. 6 by a programmable microprocessor or central processing device (CPU) 80. As is indicated in FIG. 6 by interconnection 82 between CPU 80 and battery 78, CPU 80 receives operating current from power supply 78, with power being provided only when one or more of the signal sensors 74 are activated in the previously described manner. A clock/calendar circuit 84 is connected to CPU 80 (via signal path 86 in FIG. 6) to allow time and date tagging of service tests and other information. Although not specifically shown in FIG. 6, operating power is supplied to clock/calendar 84 at all times.

In operation, CPU 80 receives and sends signals via a data bus (indicated by signal path 88 in FIG. 6), which interconnects CPU 80 with dual universal asynchronous receiver transmitters 70 and 72. The data bus 88 also interconnects CPU 80 with memory circuits, which, in the depicted embodiment, include a system read-only memory (ROM) 90, a program random access memory (RAM) 92, and an electronically erasable read-only memory (EEROM) 94. System ROM 90 can store program instructions and any data required for programming. During operation of the system, program RAM 92 provides memory space that allows CPU 80 to carry out various operations that are required for sequencing and controlling the operation of the system. In addition, RAM 92 can provide memory space that allows external programs (e.g., programs provided by clearinghouse 54) to be stored and executed. EEROM 94 allows test results and other data information to be stored and preserved until the information is no longer needed (i.e., until purposely erased by operating the system to provide an appropriate erase signal to EEROM 94).

In other embodiments of the invention, all or a portion of the functions and operations attributed to data management device 10 and/or handheld microprocessor device 12 can be performed by components or mechanisms such as a microprocessor located in the power device 15. In addition, the power device 15 may include microprocessor circuitry for generating visual display signals and signals representative of both current and past values of sensed parameters or even the service record of the power device 15. Conventional programming and design techniques can be employed to adapt commercially available units for the performance of the various functions and operations of data management device 10 and/or the handheld device 12. In arrangements in which the power device 15 includes a microprocessor that is programmed to provide signal processing in the above-described manner, the invention can use a signal interface device similar to those described above. That is, depending upon the amount of signal processing effected by the power device and the amount of signal processing performed by a microprocessor of programmable handheld device 12 (if present), the signal interface required ranges from a conventional cable (e.g., interconnection of RS232 ports) to an arrangement in which signal communication is provided with an internal or external modem, or an arrangement in which the signal interface provides only a portion of the signal processing described relative to FIGS. 4-5. Further, in another aspect of this embodiment of the invention, the display may also be integrated into the power device 15.

The invention also is capable of transmitting information to a remote location (e.g., clearinghouse 54 and/or a remotely located service provider) by means other than conventional telephone lines. For example, a modem that is configured for use with a cellular telephone system can be employed to transmit the signals provided by the modular microprocessor-based power monitoring system to a remote location via modulated RF transmission. Moreover, the invention can be employed with various digital networks such as recently developed interactive voice, video and data systems such as television systems in which a television and user interface apparatus is interactively coupled to a remote location via coaxial or fiberoptic cable and other transmission media.

Figure 7:
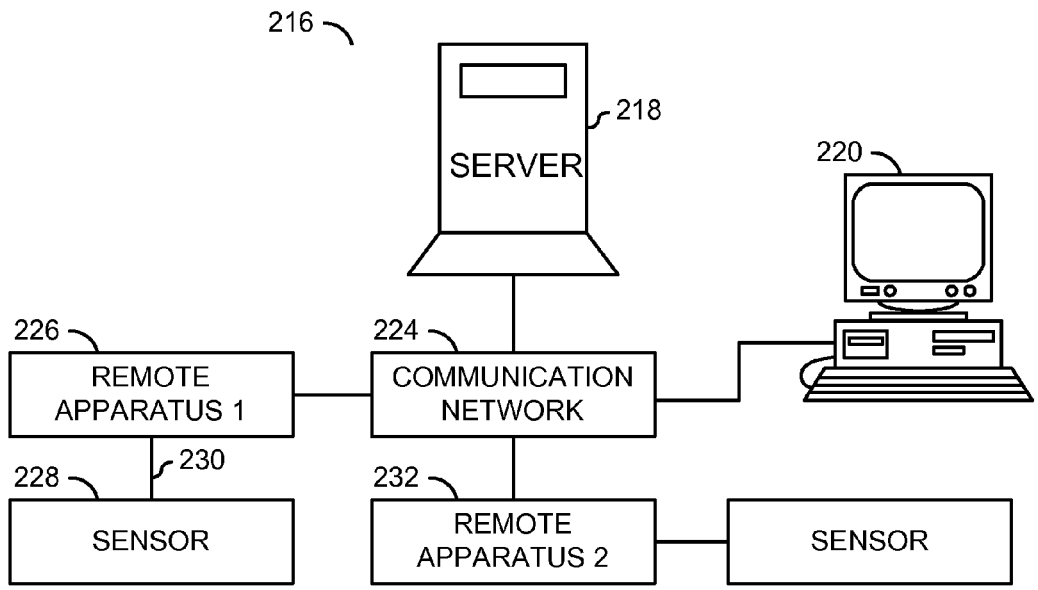
FIG. 7 is a schematic diagram of a power monitoring system according to an alternate embodiment of the invention.

Another embodiment of the invention is illustrated in FIGS. 7-17. Referring to FIG. 7, a networked system 216 includes a server 218 and a workstation 220 connected to server 218 through a communication network 224. Server 218 is preferably a world wide web server and communication network 224 is preferably the Internet. It will be apparent to one skilled in the art that server 218 may comprise a single stand-alone computer or multiple computers distributed throughout a network. Workstation 220 is preferably a personal computer, remote terminal, or web TV device connected to server 218 via the Internet. Workstation 220 functions as a remote interface for entering or selecting in server 218 messages and queries to be communicated to the power devices.

System 216 may also include first and second remotely programmable apparatuses 226 and 232 for use with first and second power devices, respectively. Each apparatus 226/232 is designed to interact with a power device in accordance with script programs received from server 218. Each apparatus 226/232 is in communication with server 218 through communication network 224, preferably the Internet. Alternatively, each apparatus 226/232 may be placed in communication with server 218 via wireless communication networks, cellular networks, telephone networks, or any other network which allows each apparatus 226/232 to exchange data with server 218. For clarity of illustration, only two apparatuses 226 and 232 are shown in FIG. 7. It is to be understood that system 216 may include any number of remotely programmable apparatuses for monitoring any number of power devices.

In one embodiment, each power device to be monitored is also provided with a sensor 228. Sensor 228 is designed to produce measurements of a parameter associated with the operation of the power device, record the measurements, and transmit the measurements to the remotely programmable apparatus 226/232 through a standard connection cable 230 as described above. Alternatively, measurements can be transmitted to the apparatus 226/232 via a wireless interface or transmission media. Examples of suitable sensors 228 include room temperature, power consumption, and humidity. Such sensors 228 are well known in the art. The specific type of sensor 228 provided to each power device is dependent upon the use of the device. For example, a humidity sensor may be supplied with an air conditioning unit to aid the operator in determining if the air conditioner should be further operated to remove excess moisture from the air.

Figure 8:
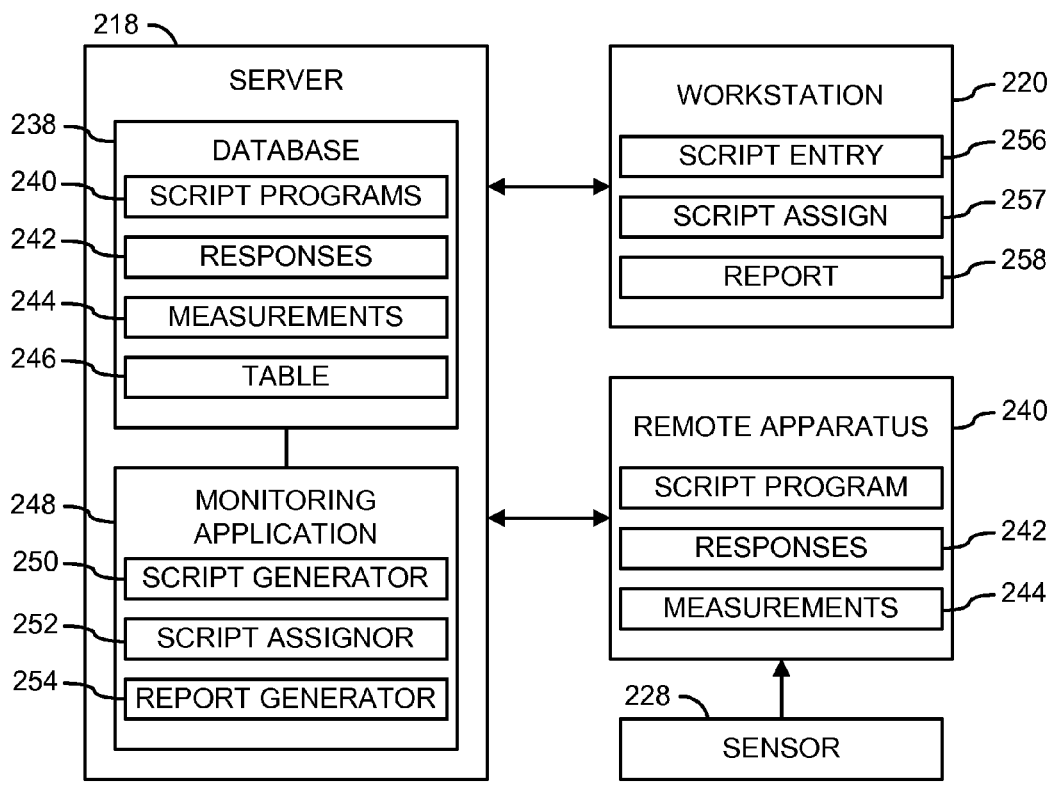
FIG. 8 is a schematic diagram illustrating the interaction of components of the embodiment of FIG. 7

FIG. 8 shows server 218, workstation 220, and apparatus 226 in greater detail. Server 218 includes a database 238 for storing script programs 240. Script programs 240 are executed by each apparatus e.g., 226/232, to communicate queries and messages to a power device operator, receive responses 242 to the queries, collect measurements 244, and to transmit responses 242 and measurements 244 to server 218. Database 238 is designed to store responses 242 and measurements 244. Database 238 further includes a look-up table 246. Table 246 contains a list of the power devices to be monitored, and for each power device, a unique power device identification code and a respective pointer to the script program assigned to the power device. Each remotely programmable apparatus, e.g., 226/232, is designed to execute assigned script programs 240 received from server 218.

Figure 9:
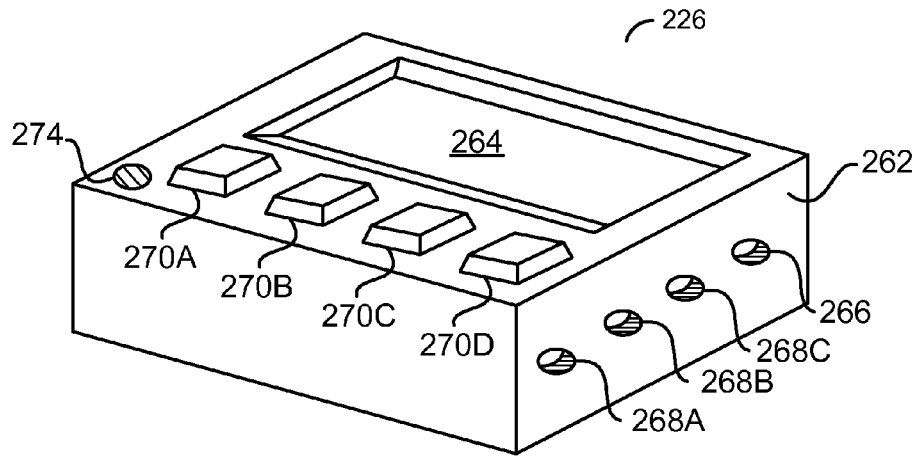
FIG. 9, is a perspective view of a remotely programmable apparatus according to one embodiment of the invention.
Figure 10:
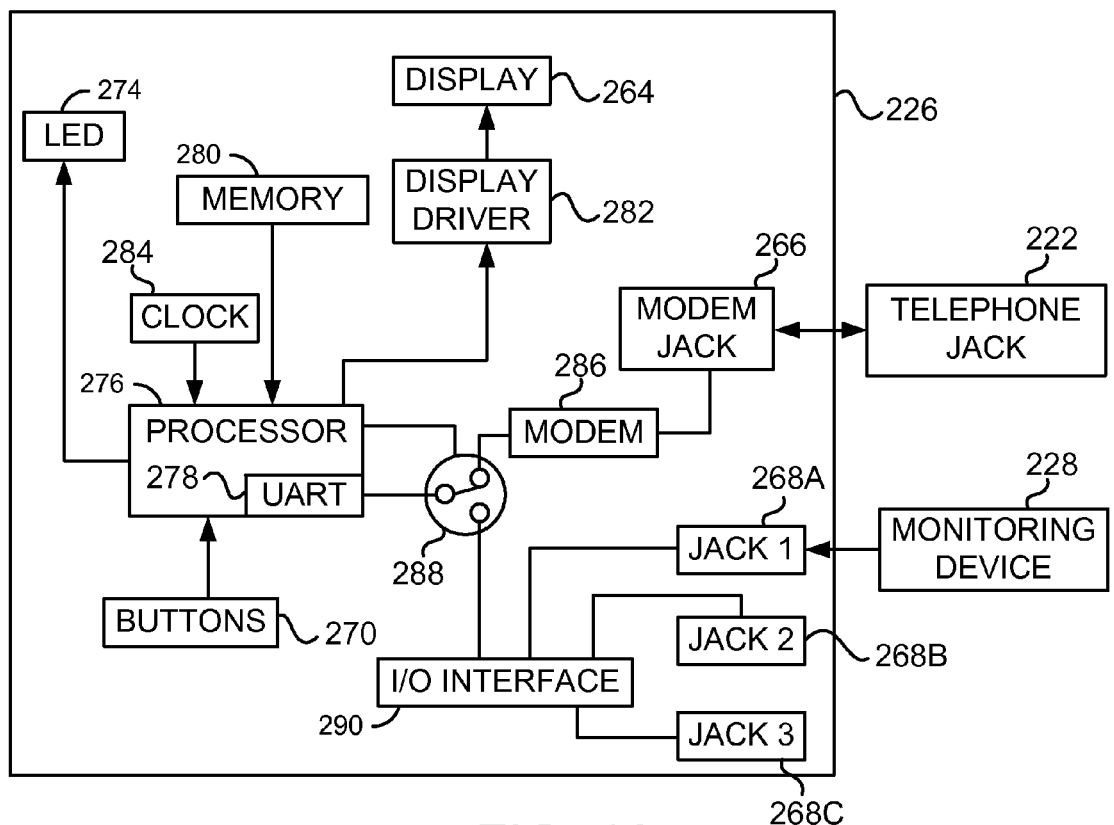
FIG. 10 is a schematic diagram of the components of the apparatus of FIG. 9.

FIGS. 9-10 show an exemplary structure of each remotely programmable apparatus according to one embodiment. For clarity, only remotely programmable apparatus 226 is shown since each remotely programmable apparatus of this embodiment can be substantially identical structure to apparatus 226. Referring to FIG. 9, apparatus 226 includes a housing 262. Housing 262 is sufficiently compact to enable apparatus 226 to be hand-held and carried by a power device operator. Apparatus 226 also includes a display 264 for displaying queries and prompts to the power device operator. In one embodiment, display 264 is a liquid crystal display (LCD).

Four user input buttons 270A, 270B, 270C, and 270D are located adjacent display 264. User input buttons 270A-D are for entering in apparatus 226 responses 242 to the queries and prompts. In the preferred embodiment, user input buttons 270A-D are momentary contact push buttons. In alternative embodiments, user input buttons 270A-D may be replaced by switches, keys, a touch sensitive display screen, or any other data input device.

Three monitoring device jacks 268A, 268B, and 268C are located on a surface of housing 262. Device jacks 268A-C are for connecting apparatus 226 to a number of sensors 228. Apparatus 226 also includes a modem jack 266 for connecting apparatus 226 to a telephone jack through a standard connection cord (not shown). Apparatus 226 further includes a visual indicator, such as a light emitting diode (LED) 274. LED 274 is for visually notifying the power device operator that he or she has unanswered queries stored in apparatus 226.

FIG. 10 is a schematic block diagram illustrating the components of apparatus 226 in greater detail. Apparatus 226 includes a microprocessor 276 and a memory 280 connected to microprocessor 276. Memory 280 is preferably a non-volatile memory, such as a serial EEPROM. Memory 280 stores script programs 240 received from server 218, measurements 244 received from sensor 228, responses 242 to queries, and the power device's unique identification code. Microprocessor 276 also includes built-in read only memory (ROM) which stores firmware for controlling the operation of apparatus 226. The firmware includes a script interpreter used by microprocessor 276 to execute script programs 240. The script interpreter interprets script commands which are executed by microprocessor 276. Specific techniques for interpreting and executing script commands in this manner are well known in the art.

Microprocessor 276 is preferably connected to memory 280 using a standard two-wire I²C interface. Microprocessor 276 is also connected to user input buttons 270, LED 274, a clock 284, and a display driver 282. Clock 284 indicates the current date and time to microprocessor 276. For clarity of illustration, clock 284 is shown as a separate component, but is preferably built into microprocessor 276. Display driver 282 operates under the control of microprocessor 276 to display information on display 264. Microprocessor 276 is preferably a PIC 16C65 processor which includes a universal asynchronous receiver transmitter (UART) 278. UART 278 is for communicating with a modem 286 and a device interface 290. A CMOS switch 288 under the control of microprocessor 276 alternately connects modem 286 and interface 290 to UART 278.

Modem 286 is connected to a telephone jack 222 through modem jack 266. Modem 286 is for exchanging data with server 218 through communication network 224. The data includes script programs 240 which are received from server 218 as well as responses 242 to queries, device measurements 244, script identification codes, and the power device's unique identification code which modem 286 transmits to server 218. Any suitable modem may be used.

Device interface 290 is connected to device jacks 268A, 268B, and 268C. Device interface 290 is for interfacing with a number of sensors 228, through device jacks 268A-C. Device interface 290 operates under the control of microprocessor 276 to collect measurements 244 from sensors 228 and to output the measurements to microprocessor 276 for storage in memory 280. In one embodiment, interface 290 is a standard RS232 interface. For simplicity of illustration, only one device interface 290 is shown in FIG. 10. However, in alternative embodiments, apparatus 226 may include multiple device interfaces to accommodate sensors 228 which have different connection standards.

Referring again to FIG. 8, server 218 includes a monitoring application 248. Monitoring application 248 is a controlling software application executed by server 218 to perform the various functions described below. Application 248 includes a script generator 250, a script assignor 252, and a report generator 254. Script generator 250 is designed to generate script programs 240 from script information entered through workstation 220. The script information is entered through a script entry screen 256. In the preferred embodiment, script entry screen 256 is implemented as a web page on server 218. Workstation 220 includes a web browser for accessing the web page to enter the script information.

Figure 11:
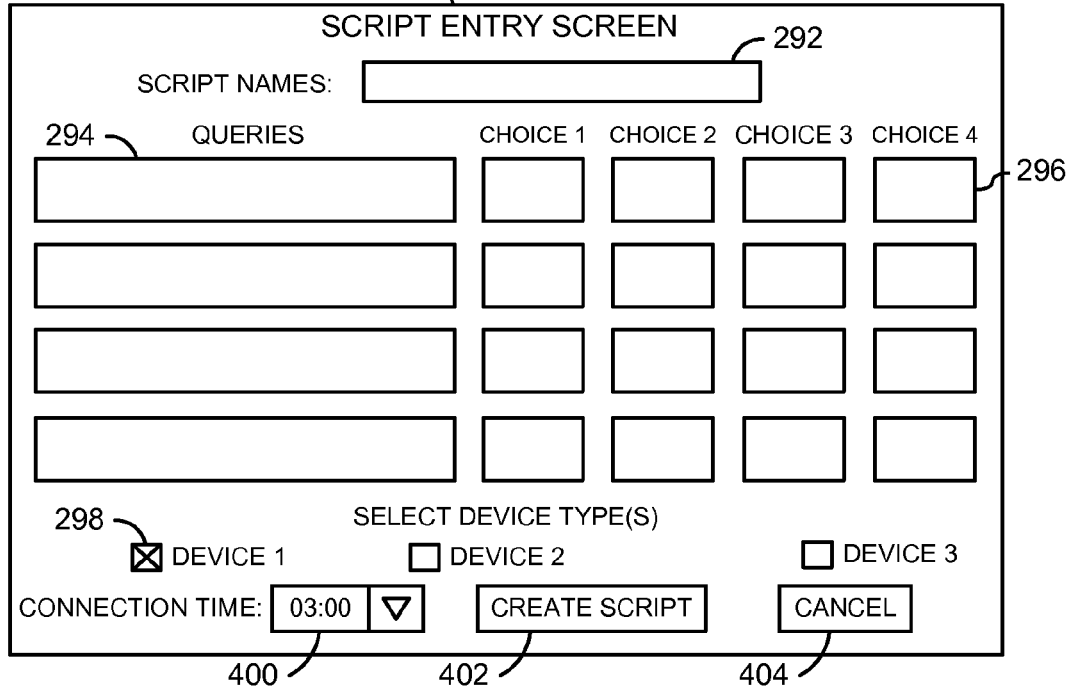
FIG. 11 is a script entry screen according to an embodiment of the invention.

FIG. 11 illustrates one embodiment of a script entry screen 256 as it appears on workstation 220. Screen 256 includes a script name field 292 for specifying the name of a script program to be generated. Screen 256 also includes entry fields 294 for entering a set of queries to be answered by a power device operator. Each entry field 294 has corresponding response choice fields 296 for entering response choices for the query. Screen 256 further includes check boxes 298 for selecting a desired power device or sensor 228 from which to collect measurements 244.

Screen 256 additionally includes a connection time field 400 for specifying a prescribed connection time at which each apparatus 226 executing the script is to establish a subsequent communication link to server 218. The connection time is preferably selected to be the time at which communication rates are the lowest, such as 3:00 AM. Screen 256 also includes a CREATE SCRIPT button 402 for instructing script generator 250 to generate a script program 240 from the information entered in screen 256. Screen 256 further includes a CANCEL button 404 for canceling the information entered in screen 256.

In one embodiment, each script program 240 created by script generator 250 conforms to the standard file format used on UNIX systems. In the standard file format, each command is listed in the upper case and followed by a colon. Every line in the script program 240 is terminated by a linefeed character {LF}, and only one command is placed on each line. The last character in the script program 240 is a UNIX end of file character {EOF}. Table 1 shows an exemplary listing of script commands used in the preferred embodiment of the invention.

TABLE 1

SCRIPT COMMANDS

| Command | Description |
|---|---|
| CLS: {LF} | Clear the display. |
| ZAP: {LF} | Erase from memory the last set of query |

TABLE 1-continued

SCRIPT COMMANDS

| Command | Description |
|---|---|
| | responses recorded. |
| LED: b{LF} | Turn the LED on or off, where b is a binary digit of 0 or 1. An argument of 1 turns on the LED, and an argument of 0 turns off the LED. |
| DISPLAY: {chars}{LF} | Display the text following the DISPLAY command. |
| INPUT: mmmm {LF} | Record a button press. The m's represent a button mask pattern for each of the four input buttons. Each m contains an "X" for disallowed buttons or an "0" for allowed buttons. For example, INPUT: 0X0X{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of one embodiment and are not intended to limit the scope of the invention. After consideration of the ensuing description, it will be apparent to one skilled in the art many other suitable scripting languages and sets of script commands may be used to implement the invention.

The script program 240 includes display commands to display the queries and response choices entered in fields 294 and 296, respectively. The script program 240 also includes input commands to receive responses 242 to the queries. The script program 240 further includes a collect command to collect device measurements 244 from the sensor 228 specified in check boxes 298. The script program 240 also includes commands to establish a subsequent communication link to server 218 at the connection time specified in field 400 FIG. 11. The steps included in the script program 240 are also shown in the flow chart of FIGS. 17A-17B and will be discussed in the operation section below.

Referring again to FIG. 8, script assignor 252 is for assigning script programs 240 to the power devices. Script programs 240 are assigned in accordance with script assignment information entered through workstation 220. The script assignment information is entered through a script assignment screen 257, which is preferably implemented as a web page on server 218.

Figure 12:
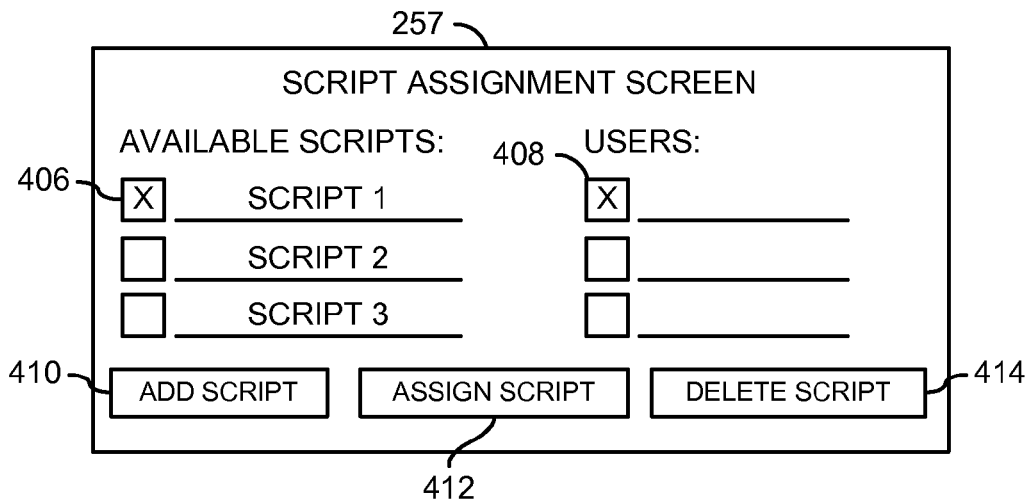
FIG. 12 is a script assignment screen according to an embodiment of the invention.
Figure 13:
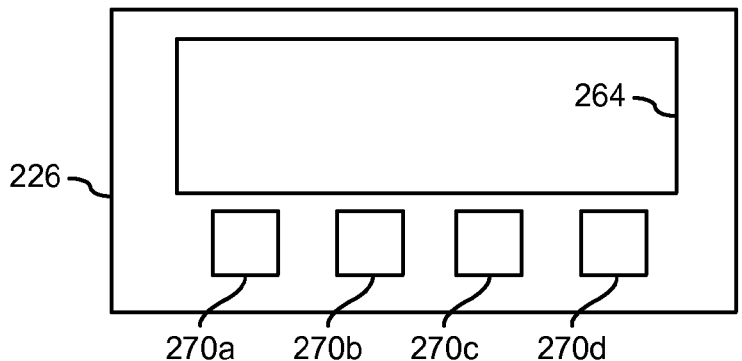
FIG. 13 is a sample query according to an embodiment of the invention.

FIG. 12 illustrates one embodiment of a sample script assignment screen 257 as it appears on workstation 220. Screen 257 includes check boxes 406 for selecting a script program 240 to be assigned, and check boxes 408 for selecting the power devices to which the script program is to be assigned. Screen 257 also includes an ASSIGN SCRIPT button 512 for entering the assignments. When button 412 is pressed, script assignor 252 creates and stores for each power device selected in check boxes 408 a respective pointer to the script program 240 selected in check boxes 406. Each pointer is stored in the power device look-up table 246 of database 238. Screen 257 further includes an ADD SCRIPT button 410 for accessing the script entry screen and a DELETE SCRIPT button 414 for deleting a script program 240. In another aspect of this embodiment of the invention, the power device may be uniquely associated with the purchaser or user of the power device.

Figure 15:
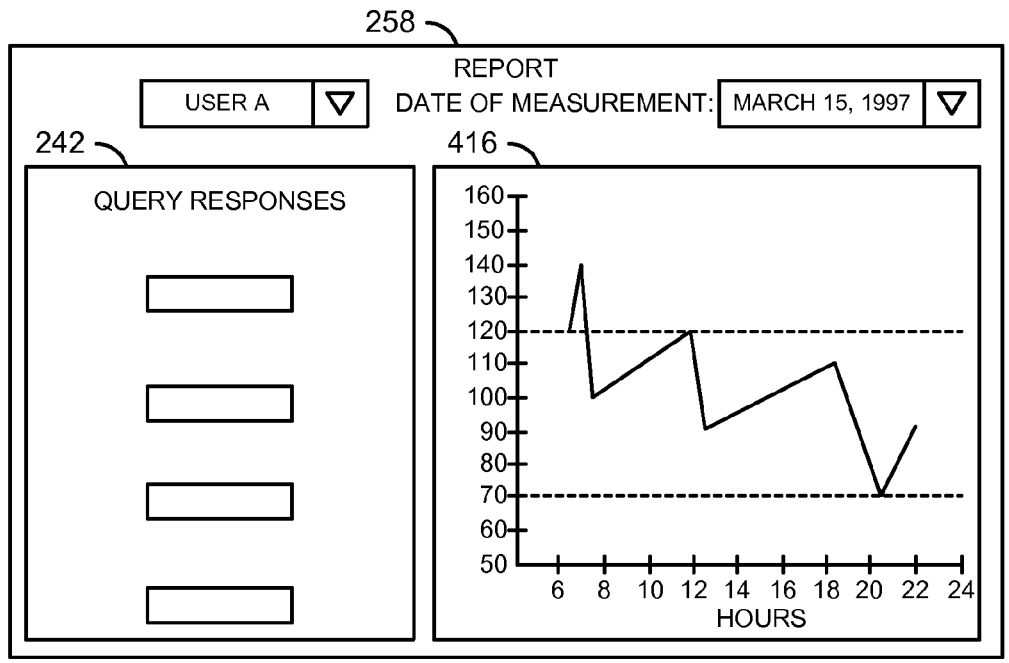
FIG. 15 is a sample report according to an embodiment of the invention.

Referring again to FIG. 8, report generator 254 is designed to generate a power device report 258 from responses 242 and device measurements 244 received in server 218. Power device report 258 is displayed on workstation 220. FIG. 15 shows a sample power device report 258 produced by report generator 254 for a selected power device. Power device report 258 includes a graph 416 of the device measurements 244 received from the power device, as well as a listing of responses 242 received from the power device operator. Specific techniques for writing a report generator program to display data in this manner are well known in the art.

Figure 16:
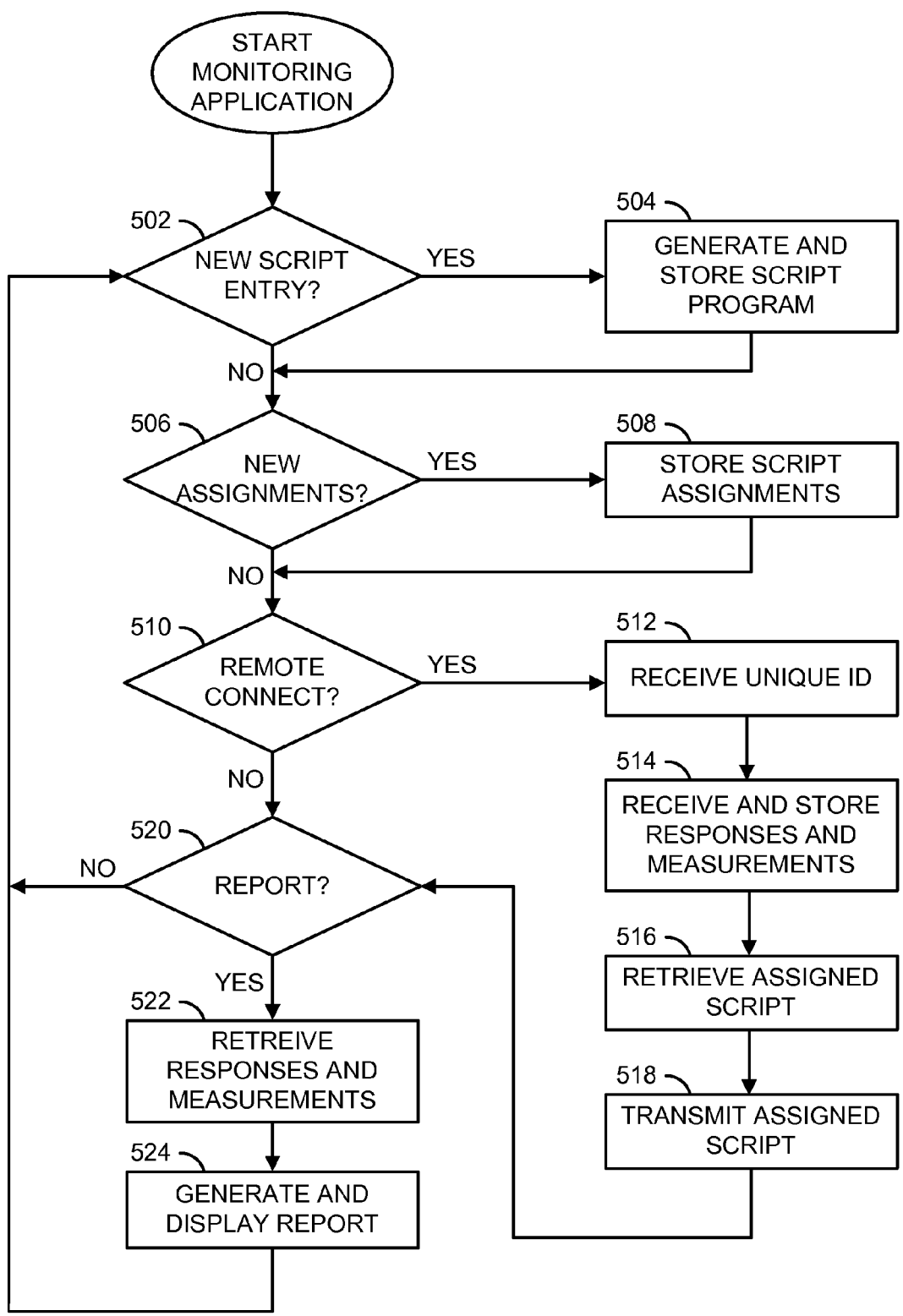
FIG. 16 is a flow chart illustrating the steps of a method of one embodiment of the invention.

The operation of one embodiment is illustrated in FIG. 16. FIG. 16 is a flow chart illustrating steps included in the monitoring application executed by server 218. In step 502, server 218 determines if new script information has been entered through script entry screen 256. If new script information has not been entered, server 218 proceeds to step 506. If new script information has been entered, server 218 proceeds to step 504.

As shown in FIG. 11, the script information includes a set of queries, and for each of the queries, corresponding response choices. The script information also includes a selected monitoring device type from which to collect device measurements 44. The script information further includes a prescribed connection time for each apparatus to establish a subsequent communication link to server 18. The script information is generally entered in server 218 by a service. Of course, any person desiring to communicate with the power device operator may also be granted access to server 218 to create and assign script programs 40. Further, it is to be understood that system 216 may include any number of remote interfaces for entering script generation and script assignment information in server 218.

In step 504, script generator 250 generates a script program from the information entered in screen 256. The script program is stored in database 238. Steps 502 and 504 are preferably repeated to generate multiple script programs, e.g. a script program for each power device. Each script program corresponds to a respective one of the sets of queries entered through script entry screen 256. Following step 504, server 218 proceeds to step 506.

In step 506, server 218 determines if new script assignment information has been entered through assignment screen 257. If new script assignment information has not been entered, server 218 proceeds to step 510. If new script assignment information has been entered, server 218 proceeds to step 508. As shown in FIG. 12 the script programs are assigned to each power device by selecting a script program through check boxes 506, selecting the power devices to whom the selected script program is to be assigned through check boxes

408, and pressing the ASSIGN SCRIPT button 412. When button 412 is pressed, script assignor 252 creates for each power device selected in check boxes 408 a respective pointer to the script program selected in check boxes 406. In step 508, each pointer is stored in look-up table 246 of database 238. Following step 508, server 218 proceeds to step 510.

In step 510, server 218 determines if any of the apparatuses are remotely connected to the server. Each power device operator to be monitored is preferably provided with his or her own remotely programmable apparatus which has the power device's unique identification code stored therein. Each power device is thus uniquely associated with a respective one of the apparatuses. If none of the apparatuses is connected, server 218 proceeds to step 520.

If an apparatus is connected, server 218 receives from the apparatus the power device's unique identification code in step 512. In step 514, server 218 receives from the apparatus the query responses 242, device measurements 244, and script identification code recorded during execution of a previously assigned script program. The script identification code identifies to server 218 which script program was executed by the apparatus to record the query responses 242 and device measurements 244. The responses, device measurements, and script identification code are stored in database 238.

In step 516, server 218 uses the power device identification code to retrieve from table 246 the pointer to the script program assigned to the power device. Server 218 then retrieves the assigned script program from database 238. In step 518, server 218 transmits the assigned script program to the power device's remotely programmable apparatus through communication network 224. Following step 518, server 218 proceeds to step 520.

In step 520, server 218 determines if a power device report request has been received from workstation 220. If no report request has been received, server 218 returns to step 502. If a report request has been received for a selected power device, server 218 retrieves from database 238 the measurements 244 and query responses 242 last received from the power device, step 522. In step 524, server 218 generates and displays power device report 258 on workstation 220. As shown in FIG. 15, report 258 includes the device measurements 244 and query responses 242 last received from the power device. Following step 524, server 218 returns to step 502.

Figure 17:
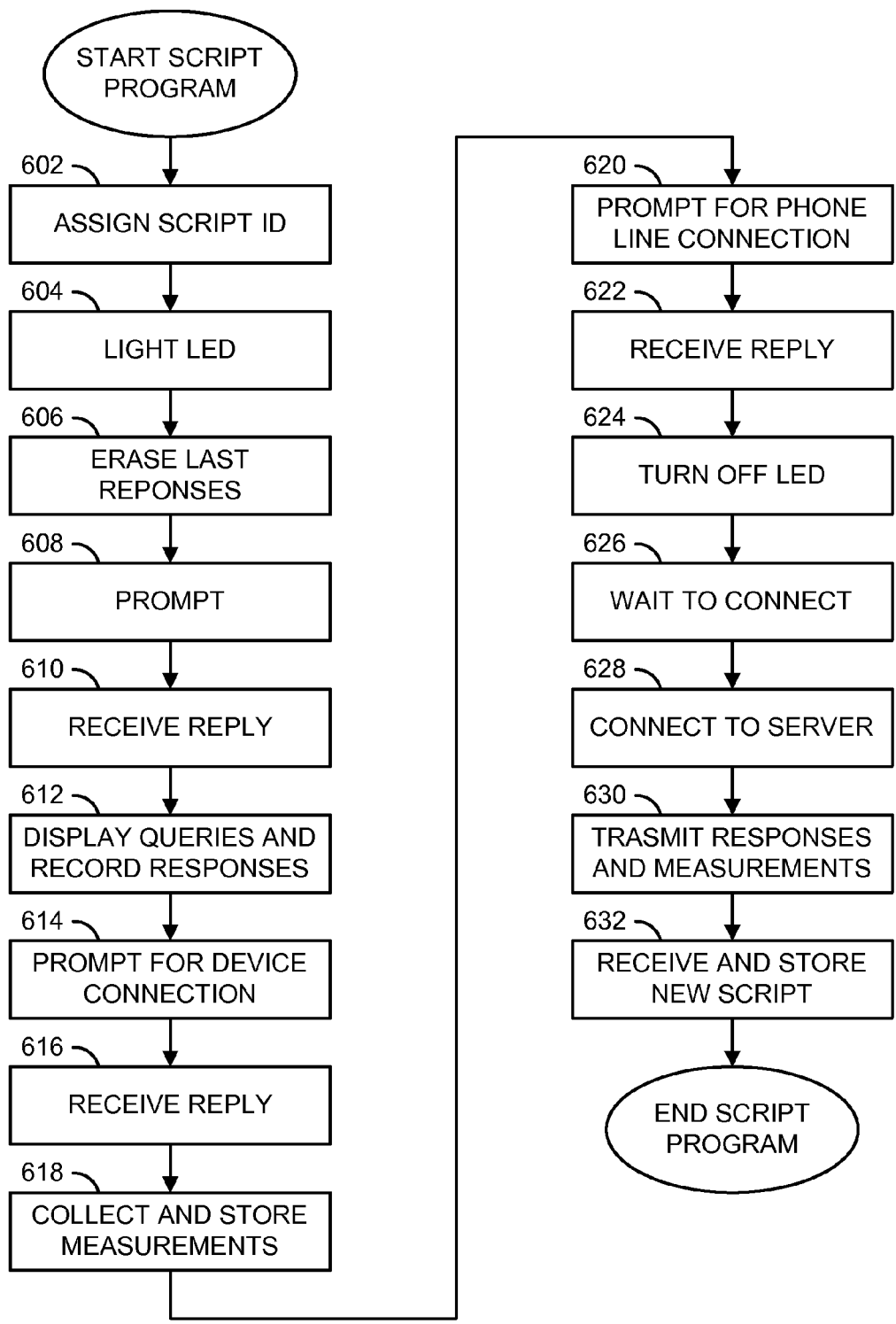
FIG. 17 is a flow chart of a sample script according to one embodiment of the invention.

FIG. 17 illustrate the steps included in the script program executed by apparatus 226. Before the script program is received, apparatus 226 is initially programmed with the power device's unique identification code and the script interpreter used by microprocessor 276 to execute the script program. The initial programming may be achieved during manufacture or during an initial connection to server 218. Following initial programming, apparatus 226 receives from server 218 the script program assigned to the power device associated with apparatus 226. The script program is received by modem 286 through a first communication link and stored in memory 280.

In step 602, microprocessor 276 assigns a script identification code to the script program and stores the script identification code in memory 280. The script identification code is subsequently transmitted to server 218 along with the query responses 242 and device measurements 244 to identify to server 218 which script program was most recently executed by apparatus 226. In step 604, microprocessor 276 lights LED 274 to notify the power device that he or she has unanswered queries stored in apparatus 226. LED 274 preferably remains lit until the queries are answered by the power device. In step 606, microprocessor 276 erases from memory 280 the last set of query responses recorded.

In step 608, microprocessor 276 prompts the power device by displaying on display 264 "ANSWER QUERIES NOW? PRESS ANY BUTTON TO START". In step 610, microprocessor 276 waits until a reply to the prompt is received from the power device operator. When a reply is received, microprocessor 276 proceeds to step 612. In step 612, microprocessor 276 executes successive display and input commands to display the queries and response choices on display 264 and to receive responses to the queries.

Figure 14:
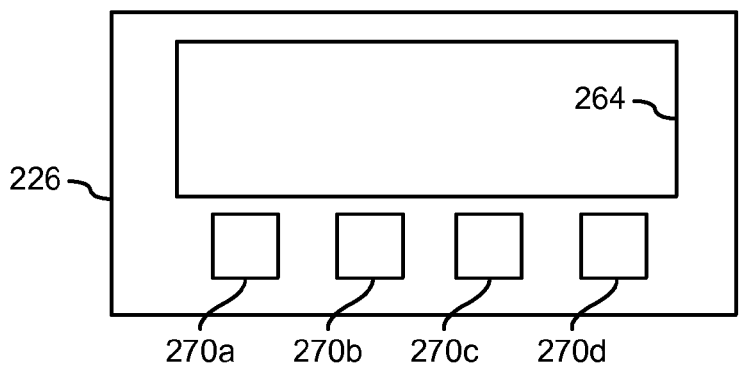
FIG. 14 is a sample prompt according to an embodiment of the invention.

In steps 614-618, microprocessor 276 executes commands to collect device measurements 244 from a selected sensor 228. The script program specifies the selected sensor 228 from which to collect the measurements. In step 614, microprocessor 276 prompts the power device to connect the selected sensor 228. A sample prompt is shown in FIG. 14. In step 616, microprocessor 276 waits until a reply to the prompt is received from the power device. When a reply is received, microprocessor 276 proceeds to step 618. Microprocessor 276 also connects UART 278 to interface 290 through switch 288. In step 618, microprocessor 276 collects device measurements 244 from sensor 228 through interface 290 measurements 244 are stored in memory 280.

In step 620, microprocessor 276 prompts the power device to connect apparatus 226 to telephone jack 222 so that apparatus 226 may connect to server 218 at the prescribed connection time. In step 622, microprocessor 276 waits until a reply to the prompt is received from the power device. When a reply is received, microprocessor 276 turns off LED 274 in step 624. In step 626, microprocessor 276 waits until it is time to connect to server 218. Microprocessor 276 compares the connection time specified in the script program to the current time output by clock 284. When it is time to connect, microprocessor 276 connects UART 278 to modem 286 through switch 288.

In step 628, microprocessor 276 establishes a subsequent communication link between apparatus 226 and server 218 through modem 286 and communication network 224. If the connection fails for any reason, microprocessor 276 repeats step 628 to get a successful connection. In step 630, microprocessor 276 transmits the device measurements 244, query responses 242, script identification code, and power device identification code stored in memory 280 to server 218 through the subsequent communication link. In step 632, microprocessor 276 receives through modem 286 a new script program from server 218. The new script program is stored in memory 280 for subsequent execution by microprocessor 276. Following step 632, the script program ends.

It should be understood that all or a portion of the operations and functionality of unit 226 may be performed by power device 15 by the incorporation of some or all of the above-described components into the power device 15.

The present invention provides many advantages. For example, the sensors built into the power devices allow remote monitoring or power consumption. With the present invention, the user can input preferences for power devices to be turned down or off in case of a power shortage. An additional advantage is that instructions can be sent to the consumer from a remote expert leading to increased energy efficiency. Further, the consumer can be supplied with educational and advertising materials. Additionally, valuable historical power usage data can be gathered to aid the consumer and power utilities in planning for future power shortages.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

I claim:

1. A system for managing power usage comprising a plurality of networked customer sites, each site comprising:
   a programmable microprocessor;
   at least one input mechanism;
   a memory having program instructions;
   a display;
   at least one power device comprising at least one sensor operable for monitoring electrical current or power consumed associated with operation of the power device and for producing signals representative of the monitored electrical current or power consumed;
   a communications device connectable in signal communication with both the programmable microprocessor and the at least one sensor; and
   the program instructions which when executed by the programmable microprocessor,
   (i) cause information stored in the memory to be presented to a first user on the display,
   (ii) collect user data from a user interaction of the first user with the at least one input mechanism in response to the information and stores the user data in the memory,
   (iii) collect sensor data from the at least one sensor and stores the sensor data in the memory,
   (iv) transmit the user data, the sensor data and an identification code of the program instructions to a remotely located server,
   (v) receive updated program instructions from the server for the programmable microprocessor, and
   (vi) store the updated program instructions in the memory,
   wherein the plurality of customer sites are configured to act as a virtual utility or power co-op.

2. The system of claim 1, wherein the virtual utility or power co-op negotiates for better power prices based on managed consumption and predictable usage patterns.

3. The system of claim 1, wherein the virtual utility or power co-op negotiates for permission-based or profile-based blackout management.

4. The system of claim 3, wherein blackout management comprises blacking out specific local usages.

5. The system of claim 1, wherein at least a portion of the plurality of networked customer sites locally generates power.

6. The system of claim 5, wherein the virtual utility or power co-op aggregates the local power generation and sells energy back to a utility.

7. The system of claim 5, wherein the local power generation comprises at least one of: solar units, wind turbines, geothermal units, fuel cells, biofuels, or exercise equipment.

8. The system of claim 1, wherein the sensors are located at electrical outlets on one or more walls of the sites.

9. The system of claim 1, wherein the power devices in the plurality of networked customer sites can be controlled remotely.

10. The system of claim 1, wherein the signals are transmitted via RF transmission.

11. The system of claim 1, further comprising software enabling authentication of a second user of the system.

12. The system of claim 11, wherein the second user comprises at least one of:
   the first user, a utility representative, or a third party.

13. The system of claim 1, further comprising at least one third party in signal communication with the server.

14. The system of claim 13, further comprising software in the server enabling authentication of the first user, a utility representative and/or the third party.

15. The system of claim 14, wherein the first user, the utility representative and/or the third party have different levels of access to the system based on the authentication.

16. A method of using a modular microprocessor system for managing power usage comprising:
   (a) at a plurality of power device sites employing at least one power device,
      (i) using program instructions stored in a non-transitory medium to generate power device related information on at least one display;
      (ii) collecting power device data using a programmable microprocessor;
      (iii) collecting user data from a first user interacting with at least one input mechanism in response to the power device related information;
   (b) connecting at least one remotely located computing facility including at least one central server for communication with a communications device at the power device sites;
   (c) providing the power device data, the user data and an identification code of the program instructions to the central server;
   (d) providing the power device data from the central server to at least one computer remotely located from and in signal communication with the central server, wherein hardware and software of the central server are configured to receive and store the power device data from the plurality of power device sites that can be viewed or retrieved by a second user from the remotely located computer; and
   (e) aggregating the plurality of power device sites into a virtual utility or power co-op.

17. The method of claim 16, wherein the aggregate of power device sites buys and/or sells power as a group.

18. The method of claim 16, wherein the aggregate of power device sites manages power within the group in order to optimize financial returns.

19. The method of claim 16, wherein the aggregate of power device sites is metered as a group with respect to a utility grid.

20. The system of claim 3, wherein the blackout management comprises blacking out specific devices.

* * * * *